US012624101B2

(12) United States Patent (10) Patent No.: US 12,624,101 B2
Djamgoz et al. (45) Date of Patent: May 12, 2026

(54) MONOCLONAL ANTIBODIES AGAINST NEONATAL Na_v1.5

(71) Applicant: Celex Oncology Innovations Limited, London (GB)

(72) Inventors: Mustafa Bilgin Ali Djamgoz, London (GB); Carsten Faltum, London (GB)

(73) Assignee: Celex Oncology Innovations Limited, London (GB)

( * ) Notice: Subject to any disclaimer, the term of this patent is extended or adjusted under 35 U.S.C. 154(b) by 965 days.

(21) Appl. No.: 17/794,083

(22) PCT Filed: Jan. 21, 2021

(86) PCT No.: PCT/EP2021/051317
§ 371 (c)(1),
(2) Date: Jul. 20, 2022

(87) PCT Pub. No.: WO2021/148524
PCT Pub. Date: Jul. 29, 2021

(65) Prior Publication Data
US 2023/0062361 A1     Mar. 2, 2023

(30) Foreign Application Priority Data
Jan. 21, 2020    (EP) ..................................... 20152789

(51) Int. Cl.
*C07K 16/28*         (2006.01)
*A61P 35/00*         (2006.01)
*C12N 15/63*         (2006.01)

(52) U.S. Cl.
CPC .............. *C07K 16/28* (2013.01); *A61P 35/00* (2018.01); *C12N 15/63* (2013.01); *C07K 2317/24* (2013.01); *C07K 2317/565* (2013.01)

(58) Field of Classification Search
None
See application file for complete search history.

(56) References Cited

U.S. PATENT DOCUMENTS

2011/0311550 A1*  12/2011  Law ...................... C07K 16/109
435/339

FOREIGN PATENT DOCUMENTS

| WO | WO 2012/049440 | 4/2012 |
| WO | WO 2018/146313 | 8/2018 |
| WO | WO 2021/078987 | 4/2021 |

OTHER PUBLICATIONS

Chen et al., Generation and analysis of random point mutations in an antibody CDR2 sequence: many mutated antibodies lose their ability to bind, 1992, Journal of Experimental Medicine, 176: 855-866. (Year: 1992).*

MacCallum et al., Antibody-antigen interactions: contact analysis and binding site topography; 1996, J. Mol. Biol., 262: 732-745. (Year: 1996).*

Koenig et al., Mutational landscape of antibody variable domains reveals a switch modulating the interdomain conformational dynamics and antigen binding; 2017, PNAS, 114(4): E486-495. (Year: 2017).*

Sano et al., In vivo breast cancer characterization imaging using two monoclonal antibodies activatably labeled with near infrared fluorophores; 2012, Breast Cancer Research, 14:R61, p. 1-8. (Year: 2012).*

Brackenbury, W., et al., "The neonatal splice variant of Nav 1.5 potentiates in vitro invasive behaviour of MDA-MB-231 human breast cancer cells," *Breast Cancer Res Treat,* 2007, vol. 101(2), pp. 149-160.

Brisson, L., et al., "Na_v1.5 Na+ channels allosterically regulate the NHE-1 exchanger and promote the activity of breast cancer cell invadopodia," *Journal of Cell Science,* 2013, vol. 126, pp. 4835-4842.

Chioni, et al., "A novel polyclonal antibody specific for the Na_v1.5 voltage-gated Na+ channel neonatal splice form," *Journal of Neuroscience Methods,* 2005, vol. 147, pp. 88-98.

Djamgoz, Mustafa B.A., "Biophysics of Cancer: Cellular Excitability ("CELEX") Hypothesis of Metastasis," *J Clin Exp Oncol,* 2014, S1, pp. 1-7.

Djamgoz, M., et al., "In Vivo Evidence for Voltage-Gated Sodium Channel Expression in Carcinomas and Potentiation of Metastasis," *Cancers,* 2019, vol. 11 (11), pp. 1-20.

Dotti, G., et al., "Design and Development of Therapies using Chimeric Antigen Receptor-Expressing T cells," *Immunol Rev.,* 2014, vol. 257(1), pp. 107-126.

Fraser, S., et al., "Predominant expression of Kv1.3 voltage-gated K+ channel subunit in rat prostate cancer cell lines: electrophysiological, pharmacological and molecular characterization," *Plugers Archinves—Eur J Physiol,* 2003, vol. 446, pp. 559-571.

Fraser, S., et al., "Voltage-Gated Sodium Channel Expression and Potentiation of Human Breast Cancer Metastasis," *Clin Cancer Res,* 2005, vol. 11(15), pp. 5381-5389, and vol. 11(22), p. 8224 (correction).

Grimes, J., et al., "Differential expression of voltage-activated Na+ currents in two prostatic tumour cell lines: contribution to invasiveness in vitro," *FEBS Letters,* 1995, vol. 369, pp. 290-294.

(Continued)

*Primary Examiner* — Daniel E Kolker
*Assistant Examiner* — James Ryland Melchior
(74) *Attorney, Agent, or Firm* — Womble Bond Dickinson (US) LLP

(57) ABSTRACT

Describe herein are binding molecules which specifically bind to neonatal 5'-exon splice variants of the a subunit of Na_v1.5 (nNa_v1.5), including monoclonal antibodies and antigen-binding fragments, bispecific antibodies and antibody-drug conjugates derived from such monoclonal antibodies, and NK and T cells comprising chimeric antigen receptors derived from such monoclonal antibodies, and their use in diagnostic and therapeutic methods.

18 Claims, 4 Drawing Sheets

Specification includes a Sequence Listing.

(56)	References Cited

OTHER PUBLICATIONS

Laniadio, M., et al., "Expression and Functional Analysis of Voltage-Activated Na$^+$ Channels in Human Prostate Cancer Cell Lines and their Contribution to Invasion in Vitro," *AJP*, 1997, vol. 150(4), pp. 1213-1221.

Laniado, M., et al., "Voltage-Gated K$^+$ Channel Activity in Human Prostate Cancer Cell Lines of Markedly Different Metastatic Potential: Distinguishing Characteristics of PC-3 and LNCaP Cells," *The Prostate*, 2001, vol. 46, pp. 262-274.

Onkal, R., et al., "Alternative Splicing of Nav.5: An Electrophysiological Comparison of 'Neonatal' and 'Adult' Isoforms and Critical Involvement of a Lysine Residue," *Journal of Cellular Physiology*, 2008, vol. 216, pp. 716-726.

Onkal, R., et al., "Molecular pharmacology of voltage-gated sodium channel expression in metastatic disease: Clinical potential of neonatal Nav1.5 in breast cancer," *European Journal of Pharmacology*, 2009, vol. 625(1-3), pp. 206-219.

Sadelain, M., et al., "The basic principles of chimeric antigen receptor (CAR) design," *Cancer Discov*, 2013, vol. 3(4), pp. 388-398.

* cited by examiner

VH sequence (SEQ ID NO:12)

| Q | V | T | L | K | V | S | G | P | G | L | L | Q | P | S | Q | T | L | S | L |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |

| T | C | S | F | S | G | S | L | T | S | L | S | G | M | G | V | S | W | I | R |
|---|---|---|---|---|---|---|---|---|---|---|---|---|---|---|---|---|---|---|---|
| 21 | 22 | 23 | 24 | 25 | 26 | 27 | 28 | 29 | 30 | 31 | 32 | 33 | 34 | 35 | 35A | 35B | 36 | 37 | 38 |

| Q | A | A | G | K | G | L | E | W | L | A | H | I | Y | W | D | D | D | K | R |
|---|---|---|---|---|---|---|---|---|---|---|---|---|---|---|---|---|---|---|---|
| 39 | 40 | 41 | 42 | 43 | 44 | 45 | 46 | 47 | 48 | 49 | 50 | 51 | 52 | 53 | 54 | 55 | 56 | 57 | 58 |

| Y | N | P | A | L | K | S | R | L | T | I | S | K | D | T | S | S | N | Q | V |
|---|---|---|---|---|---|---|---|---|---|---|---|---|---|---|---|---|---|---|---|
| 59 | 60 | 61 | 62 | 63 | 64 | 65 | 66 | 67 | 68 | 69 | 70 | 71 | 72 | 73 | 74 | 75 | 76 | 77 | 78 |

| F | L | N | I | T | S | V | D | T | A | D | T | A | T | Y | Y | C | A | R | R |
|---|---|---|---|---|---|---|---|---|---|---|---|---|---|---|---|---|---|---|---|
| 79 | 80 | 81 | 82 | 82A | 82B | 82C | 83 | 84 | 85 | 86 | 87 | 88 | 89 | 90 | 91 | 92 | 93 | 94 | 95 |

| E | D | Y | V | T | S | L | L | S | G | A | K | G | L | W | S | L | C | L |
|---|---|---|---|---|---|---|---|---|---|---|---|---|---|---|---|---|---|---|---|
| 96 | 97 | 98 | 99 | 100 | 100A | 101 | 102 | 103 | 104 | 105 | 106 | 107 | 108 | 109 | 110 | 111 | 112 | 113 |

Fig. 4a

VL sequence (SEQ ID NO:13)

| D | I | V | L | T | Q | S | P | A | S | L | A | V | S | L | G | Q | R | A | S |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |

| I | S | Y | R | A | S | K | S | V | S | T | S | G | Y | M | H | W | N |
|---|---|---|---|---|---|---|---|---|---|---|---|---|---|---|---|---|---|
| 21 | 22 | 23 | 24 | 25 | 26 | 27 | 28 | 29 | 30 | 30A | 30B | 30C | 30D | 31 | 32 | 33 | 34 | 35 | 36 |

| R | Q | K | P | G | Q | P | P | R | L | L | I | Y | L | V | S | N | L | E | S |
|---|---|---|---|---|---|---|---|---|---|---|---|---|---|---|---|---|---|---|---|
| 37 | 38 | 39 | 40 | 41 | 42 | 43 | 44 | 45 | 46 | 47 | 48 | 49 | 50 | 51 | 52 | 53 | 54 | 55 | 56 |

| G | V | P | A | R | F | S | G | S | G | S | G | T | D | F | T | L | N | I | H |
|---|---|---|---|---|---|---|---|---|---|---|---|---|---|---|---|---|---|---|---|
| 57 | 58 | 59 | 60 | 61 | 62 | 63 | 64 | 65 | 66 | 67 | 68 | 69 | 70 | 71 | 72 | 73 | 74 | 75 | 76 |

| P | V | E | E | D | A | A | T | Y | Y | C | Q | H | I | R | E | L | T | R |
|---|---|---|---|---|---|---|---|---|---|---|---|---|---|---|---|---|---|---|---|
| 77 | 78 | 79 | 80 | 81 | 82 | 83 | 84 | 85 | 86 | 87 | 88 | 89 | 90 | 91 | 92 | 93 | 94 | 95 | 95A |

| S | E | G | G | P | S | W | K | Y | D |
|---|---|---|---|---|---|---|---|---|---|
| 96 | 97 | 98 | 99 | 100 | 101 | 102 | 103 | 104 | 105 |

Fig. 4b

```
SEQUENCE LISTING

<160> NUMBER OF SEQ ID NOS: 19

<210> SEQ ID NO 1
<211> LENGTH: 2016
<212> TYPE: PRT
<213> ORGANISM: Homo sapiens

<400> SEQUENCE: 1

Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
            115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
            195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
            275                 280                 285

Gly Thr Asn Gly Ser Val Glu Ala Asp Gly Leu Val Trp Glu Ser Leu
```

-continued

```
         290                295                300

Asp Leu Tyr Leu Ser Asp Pro Glu Asn Tyr Leu Leu Lys Asn Gly Thr
305                310                315                320

Ser Asp Val Leu Leu Cys Gly Asn Ser Ser Asp Ala Gly Thr Cys Pro
              325                330                335

Glu Gly Tyr Arg Cys Leu Lys Ala Gly Glu Asn Pro Asp His Gly Tyr
              340                345                350

Thr Ser Phe Asp Ser Phe Ala Trp Ala Phe Leu Ala Leu Phe Arg Leu
              355                360                365

Met Thr Gln Asp Cys Trp Glu Arg Leu Tyr Gln Gln Thr Leu Arg Ser
    370                375                380

Ala Gly Lys Ile Tyr Met Ile Phe Phe Met Leu Val Ile Phe Leu Gly
385                390                395                400

Ser Phe Tyr Leu Val Asn Leu Ile Leu Ala Val Val Ala Met Ala Tyr
              405                410                415

Glu Glu Gln Asn Gln Ala Thr Ile Ala Glu Thr Glu Glu Lys Glu Lys
              420                425                430

Arg Phe Gln Glu Ala Met Glu Met Leu Lys Lys Glu His Glu Ala Leu
              435                440                445

Thr Ile Arg Gly Val Asp Thr Val Ser Arg Ser Ser Leu Glu Met Ser
    450                455                460

Pro Leu Ala Pro Val Asn Ser His Glu Arg Arg Ser Lys Arg Arg Lys
465                470                475                480

Arg Met Ser Ser Gly Thr Glu Glu Cys Gly Glu Asp Arg Leu Pro Lys
              485                490                495

Ser Asp Ser Glu Asp Gly Pro Arg Ala Met Asn His Leu Ser Leu Thr
              500                505                510

Arg Gly Leu Ser Arg Thr Ser Met Lys Pro Arg Ser Ser Arg Gly Ser
              515                520                525

Ile Phe Thr Phe Arg Arg Arg Asp Leu Gly Ser Glu Ala Asp Phe Ala
    530                535                540

Asp Asp Glu Asn Ser Thr Ala Gly Glu Ser Glu Ser His His Thr Ser
545                550                555                560

Leu Leu Val Pro Trp Pro Leu Arg Arg Thr Ser Ala Gln Gly Gln Pro
              565                570                575

Ser Pro Gly Thr Ser Ala Pro Gly His Ala Leu His Gly Lys Lys Asn
              580                585                590

Ser Thr Val Asp Cys Asn Gly Val Val Ser Leu Leu Gly Ala Gly Asp
              595                600                605

Pro Glu Ala Thr Ser Pro Gly Ser His Leu Leu Arg Pro Val Met Leu
    610                615                620

Glu His Pro Pro Asp Thr Thr Thr Pro Ser Glu Glu Pro Gly Gly Pro
625                630                635                640

Gln Met Leu Thr Ser Gln Ala Pro Cys Val Asp Gly Phe Glu Glu Pro
              645                650                655

Gly Ala Arg Gln Arg Ala Leu Ser Ala Val Ser Val Leu Thr Ser Ala
              660                665                670

Leu Glu Glu Leu Glu Glu Ser Arg His Lys Cys Pro Pro Cys Trp Asn
              675                680                685

Arg Leu Ala Gln Arg Tyr Leu Ile Trp Glu Cys Cys Pro Leu Trp Met
    690                695                700

Ser Ile Lys Gln Gly Val Lys Leu Val Val Met Asp Pro Phe Thr Asp
705                710                715                720
```

Leu Thr Ile Thr Met Cys Ile Val Leu Asn Thr Leu Phe Met Ala Leu
            725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
            805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
            885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
    930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln  Leu Pro Ser Cys Ile  Ala Thr Pro
            995                 1000                1005

Tyr Ser  Pro Pro Pro Glu  Thr Glu Lys Val Pro  Pro Thr Arg
    1010        1015                 1020

Lys Glu  Thr Arg Phe Glu Glu  Gly Glu Gln Pro Gly  Gln Gly Thr
    1025            1030                 1035

Pro Gly  Asp Pro Glu Pro Val  Cys Val Pro Ile Ala  Val Ala Glu
    1040            1045                 1050

Ser Asp  Thr Asp Asp Gln Glu  Glu Asp Glu Glu Asn  Ser Leu Gly
    1055            1060                 1065

Thr Glu  Glu Glu Ser Ser Lys  Gln Gln Glu Ser Gln  Pro Val Ser
    1070            1075                 1080

Gly Gly  Pro Glu Ala Pro Pro  Asp Ser Arg Thr Trp  Ser Gln Val
    1085            1090                 1095

Ser Ala  Thr Ala Ser Ser Glu  Ala Glu Ala Ser Ala  Ser Gln Ala
    1100            1105                 1110

Asp Trp  Arg Gln Gln Trp Lys  Ala Glu Pro Gln Ala  Pro Gly Cys
    1115            1120                 1125

-continued

```
Gly Glu  Thr Pro Glu Asp Ser  Cys Ser Glu Gly Ser  Thr Ala Asp
    1130                 1135             1140

Met Thr  Asn Thr Ala Glu Leu  Leu Glu Gln Ile Pro  Asp Leu Gly
    1145                 1150             1155

Gln Asp  Val Lys Asp Pro Glu  Asp Cys Phe Thr Glu  Gly Cys Val
    1160                 1165             1170

Arg Arg  Cys Pro Cys Cys Ala  Val Asp Thr Thr Gln  Ala Pro Gly
    1175                 1180             1185

Lys Val  Trp Trp Arg Leu Arg  Lys Thr Cys Tyr His  Ile Val Glu
    1190                 1195             1200

His Ser  Trp Phe Glu Thr Phe  Ile Ile Phe Met Ile  Leu Leu Ser
    1205                 1210             1215

Ser Gly  Ala Leu Ala Phe Glu  Asp Ile Tyr Leu Glu  Glu Arg Lys
    1220                 1225             1230

Thr Ile  Lys Val Leu Leu Glu  Tyr Ala Asp Lys Met  Phe Thr Tyr
    1235                 1240             1245

Val Phe  Val Leu Glu Met Leu  Leu Lys Trp Val Ala  Tyr Gly Phe
    1250                 1255             1260

Lys Lys  Tyr Phe Thr Asn Ala  Trp Cys Trp Leu Asp  Phe Leu Ile
    1265                 1270             1275

Val Asp  Val Ser Leu Val Ser  Leu Val Ala Asn Thr  Leu Gly Phe
    1280                 1285             1290

Ala Glu  Met Gly Pro Ile Lys  Ser Leu Arg Thr Leu  Arg Ala Leu
    1295                 1300             1305

Arg Pro  Leu Arg Ala Leu Ser  Arg Phe Glu Gly Met  Arg Val Val
    1310                 1315             1320

Val Asn  Ala Leu Val Gly Ala  Ile Pro Ser Ile Met  Asn Val Leu
    1325                 1330             1335

Leu Val  Cys Leu Ile Phe Trp  Leu Ile Phe Ser Ile  Met Gly Val
    1340                 1345             1350

Asn Leu  Phe Ala Gly Lys Phe  Gly Arg Cys Ile Asn  Gln Thr Glu
    1355                 1360             1365

Gly Asp  Leu Pro Leu Asn Tyr  Thr Ile Val Asn Asn  Lys Ser Gln
    1370                 1375             1380

Cys Glu  Ser Leu Asn Leu Thr  Gly Glu Leu Tyr Trp  Thr Lys Val
    1385                 1390             1395

Lys Val  Asn Phe Asp Asn Val  Gly Ala Gly Tyr Leu  Ala Leu Leu
    1400                 1405             1410

Gln Val  Ala Thr Phe Lys Gly  Trp Met Asp Ile Met  Tyr Ala Ala
    1415                 1420             1425

Val Asp  Ser Arg Gly Tyr Glu  Glu Gln Pro Gln Trp  Glu Tyr Asn
    1430                 1435             1440

Leu Tyr  Met Tyr Ile Tyr Phe  Val Ile Phe Ile Ile  Phe Gly Ser
    1445                 1450             1455

Phe Phe  Thr Leu Asn Leu Phe  Ile Gly Val Ile Ile  Asp Asn Phe
    1460                 1465             1470

Asn Gln  Gln Lys Lys Lys Leu  Gly Gly Gln Asp Ile  Phe Met Thr
    1475                 1480             1485

Glu Glu  Gln Lys Lys Tyr Tyr  Asn Ala Met Lys Lys  Leu Gly Ser
    1490                 1495             1500

Lys Lys  Pro Gln Lys Pro Ile  Pro Arg Pro Leu Asn  Lys Tyr Gln
    1505                 1510             1515

Gly Phe  Ile Phe Asp Ile Val  Thr Lys Gln Ala Phe  Asp Val Thr
```

-continued

```
        1520                1525                1530

Ile Met  Phe Leu Ile Cys Leu  Asn Met Val Thr Met  Met Val Glu
    1535                1540                1545

Thr Asp  Asp Gln Ser Pro Glu  Lys Ile Asn Ile Leu  Ala Lys Ile
    1550                1555                1560

Asn Leu  Leu Phe Val Ala Ile  Phe Thr Gly Glu Cys  Ile Val Lys
    1565                1570                1575

Leu Ala  Ala Leu Arg His Tyr  Tyr Phe Thr Asn Ser  Trp Asn Ile
    1580                1585                1590

Phe Asp  Phe Val Val Val Ile  Leu Ser Ile Val Gly  Thr Val Leu
    1595                1600                1605

Ser Asp  Ile Ile Gln Lys Tyr  Phe Phe Ser Pro Thr  Leu Phe Arg
    1610                1615                1620

Val Ile  Arg Leu Ala Arg Ile  Gly Arg Ile Leu Arg  Leu Ile Arg
    1625                1630                1635

Gly Ala  Lys Gly Ile Arg Thr  Leu Leu Phe Ala Leu  Met Met Ser
    1640                1645                1650

Leu Pro  Ala Leu Phe Asn Ile  Gly Leu Leu Leu Phe  Leu Val Met
    1655                1660                1665

Phe Ile  Tyr Ser Ile Phe Gly  Met Ala Asn Phe Ala  Tyr Val Lys
    1670                1675                1680

Trp Glu  Ala Gly Ile Asp Asp  Met Phe Asn Phe Gln  Thr Phe Ala
    1685                1690                1695

Asn Ser  Met Leu Cys Leu Phe  Gln Ile Thr Thr Ser  Ala Gly Trp
    1700                1705                1710

Asp Gly  Leu Leu Ser Pro Ile  Leu Asn Thr Gly Pro  Pro Tyr Cys
    1715                1720                1725

Asp Pro  Thr Leu Pro Asn Ser  Asn Gly Ser Arg Gly  Asp Cys Gly
    1730                1735                1740

Ser Pro  Ala Val Gly Ile Leu  Phe Phe Thr Thr Tyr  Ile Ile Ile
    1745                1750                1755

Ser Phe  Leu Ile Val Val Asn  Met Tyr Ile Ala Ile  Ile Leu Glu
    1760                1765                1770

Asn Phe  Ser Val Ala Thr Glu  Glu Ser Thr Glu Pro  Leu Ser Glu
    1775                1780                1785

Asp Asp  Phe Asp Met Phe Tyr  Glu Ile Trp Glu Lys  Phe Asp Pro
    1790                1795                1800

Glu Ala  Thr Gln Phe Ile Glu  Tyr Ser Val Leu Ser  Asp Phe Ala
    1805                1810                1815

Asp Ala  Leu Ser Glu Pro Leu  Arg Ile Ala Lys Pro  Asn Gln Ile
    1820                1825                1830

Ser Leu  Ile Asn Met Asp Leu  Pro Met Val Ser Gly  Asp Arg Ile
    1835                1840                1845

His Cys  Met Asp Ile Leu Phe  Ala Phe Thr Lys Arg  Val Leu Gly
    1850                1855                1860

Glu Ser  Gly Glu Met Asp Ala  Leu Lys Ile Gln Met  Glu Glu Lys
    1865                1870                1875

Phe Met  Ala Ala Asn Pro Ser  Lys Ile Ser Tyr Glu  Pro Ile Thr
    1880                1885                1890

Thr Thr  Leu Arg Arg Lys His  Glu Glu Val Ser Ala  Met Val Ile
    1895                1900                1905

Gln Arg  Ala Phe Arg Arg His  Leu Leu Gln Arg Ser  Leu Lys His
    1910                1915                1920
```

```
Ala Ser  Phe Leu Phe Arg Gln  Gln Ala Gly Ser Gly  Leu Ser Glu
    1925             1930             1935

Glu Asp  Ala Pro Glu Arg Glu  Gly Leu Ile Ala Tyr  Val Met Ser
    1940             1945             1950

Glu Asn  Phe Ser Arg Pro Leu  Gly Pro Pro Ser Ser  Ser Ser Ile
    1955             1960             1965

Ser Ser  Thr Ser Phe Pro Pro  Ser Tyr Asp Ser Val  Thr Arg Ala
    1970             1975             1980

Thr Ser  Asp Asn Leu Gln Val  Arg Gly Ser Asp Tyr  Ser His Ser
    1985             1990             1995

Glu Asp  Leu Ala Asp Phe Pro  Pro Ser Pro Asp Arg  Asp Arg Glu
    2000             2005             2010

Ser Ile  Val
    2015

<210> SEQ ID NO 2
<211> LENGTH: 2016
<212> TYPE: PRT
<213> ORGANISM: Homo sapiens

<400> SEQUENCE: 2

Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Val Ser Glu
        195                 200                 205

Asn Ile Lys Leu Gly Asn Leu Ser Ala Leu Arg Thr Phe Arg Val Leu
    210                 215                 220

Arg Ala Leu Lys Thr Ile Ser Val Ile Pro Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
```

-continued

```
            260              265                270

Met Gly Asn Leu Arg His Lys Cys Val Arg Asn Phe Thr Ala Leu Asn
            275              280                285

Gly Thr Asn Gly Ser Val Glu Ala Asp Gly Leu Val Trp Glu Ser Leu
            290              295                300

Asp Leu Tyr Leu Ser Asp Pro Glu Asn Tyr Leu Leu Lys Asn Gly Thr
305              310              315                320

Ser Asp Val Leu Leu Cys Gly Asn Ser Ser Asp Ala Gly Thr Cys Pro
            325              330                335

Glu Gly Tyr Arg Cys Leu Lys Ala Gly Glu Asn Pro Asp His Gly Tyr
            340              345                350

Thr Ser Phe Asp Ser Phe Ala Trp Ala Phe Leu Ala Leu Phe Arg Leu
            355              360                365

Met Thr Gln Asp Cys Trp Glu Arg Leu Tyr Gln Gln Thr Leu Arg Ser
            370              375                380

Ala Gly Lys Ile Tyr Met Ile Phe Phe Met Leu Val Ile Phe Leu Gly
385              390              395                400

Ser Phe Tyr Leu Val Asn Leu Ile Leu Ala Val Val Ala Met Ala Tyr
            405              410                415

Glu Glu Gln Asn Gln Ala Thr Ile Ala Glu Thr Glu Glu Lys Glu Lys
            420              425                430

Arg Phe Gln Glu Ala Met Glu Met Leu Lys Lys Glu His Glu Ala Leu
            435              440                445

Thr Ile Arg Gly Val Asp Thr Val Ser Arg Ser Ser Leu Glu Met Ser
            450              455                460

Pro Leu Ala Pro Val Asn Ser His Glu Arg Arg Ser Lys Arg Arg Lys
465              470              475                480

Arg Met Ser Ser Gly Thr Glu Glu Cys Gly Glu Asp Arg Leu Pro Lys
            485              490                495

Ser Asp Ser Glu Asp Gly Pro Arg Ala Met Asn His Leu Ser Leu Thr
            500              505                510

Arg Gly Leu Ser Arg Thr Ser Met Lys Pro Arg Ser Ser Arg Gly Ser
            515              520                525

Ile Phe Thr Phe Arg Arg Arg Asp Leu Gly Ser Glu Ala Asp Phe Ala
            530              535                540

Asp Asp Glu Asn Ser Thr Ala Gly Glu Ser Glu Ser His His Thr Ser
545              550              555                560

Leu Leu Val Pro Trp Pro Leu Arg Arg Thr Ser Ala Gln Gly Gln Pro
            565              570                575

Ser Pro Gly Thr Ser Ala Pro Gly His Ala Leu His Gly Lys Lys Asn
            580              585                590

Ser Thr Val Asp Cys Asn Gly Val Val Ser Leu Leu Gly Ala Gly Asp
            595              600                605

Pro Glu Ala Thr Ser Pro Gly Ser His Leu Leu Arg Pro Val Met Leu
            610              615                620

Glu His Pro Pro Asp Thr Thr Thr Pro Ser Glu Glu Pro Gly Gly Pro
625              630              635                640

Gln Met Leu Thr Ser Gln Ala Pro Cys Val Asp Gly Phe Glu Glu Pro
            645              650                655

Gly Ala Arg Gln Arg Ala Leu Ser Ala Val Ser Val Leu Thr Ser Ala
            660              665                670

Leu Glu Glu Leu Glu Glu Ser Arg His Lys Cys Pro Pro Cys Trp Asn
            675              680                685
```

-continued

```
Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
    930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln  Leu Pro Ser Cys Ile  Ala Thr Pro
        995                 1000                1005

Tyr Ser  Pro Pro Pro Pro Glu  Thr Glu Lys Val Pro  Pro Thr Arg
    1010                1015                1020

Lys Glu  Thr Arg Phe Glu Glu  Gly Glu Gln Pro Gly  Gln Gly Thr
    1025                1030                1035

Pro Gly  Asp Pro Glu Pro Val  Cys Val Pro Ile Ala  Val Ala Glu
    1040                1045                1050

Ser Asp  Thr Asp Asp Gln Glu  Glu Asp Glu Glu Asn  Ser Leu Gly
    1055                1060                1065

Thr Glu  Glu Glu Ser Ser Lys  Gln Gln Glu Ser Gln  Pro Val Ser
    1070                1075                1080

Gly Gly  Pro Glu Ala Pro Pro  Asp Ser Arg Thr Trp  Ser Gln Val
    1085                1090                1095
```

```
Ser Ala  Thr Ala Ser Ser Glu  Ala Glu Ala Ser Ala  Ser Gln Ala
    1100             1105             1110

Asp Trp  Arg Gln Gln Trp Lys  Ala Glu Pro Gln Ala  Pro Gly Cys
    1115             1120             1125

Gly Glu  Thr Pro Glu Asp Ser  Cys Ser Glu Gly Ser  Thr Ala Asp
    1130             1135             1140

Met Thr  Asn Thr Ala Glu Leu  Leu Glu Gln Ile Pro  Asp Leu Gly
    1145             1150             1155

Gln Asp  Val Lys Asp Pro Glu  Asp Cys Phe Thr Glu  Gly Cys Val
    1160             1165             1170

Arg Arg  Cys Pro Cys Cys Ala  Val Asp Thr Thr Gln  Ala Pro Gly
    1175             1180             1185

Lys Val  Trp Trp Arg Leu Arg  Lys Thr Cys Tyr His  Ile Val Glu
    1190             1195             1200

His Ser  Trp Phe Glu Thr Phe  Ile Ile Phe Met Ile  Leu Leu Ser
    1205             1210             1215

Ser Gly  Ala Leu Ala Phe Glu  Asp Ile Tyr Leu Glu  Glu Arg Lys
    1220             1225             1230

Thr Ile  Lys Val Leu Leu Glu  Tyr Ala Asp Lys Met  Phe Thr Tyr
    1235             1240             1245

Val Phe  Val Leu Glu Met Leu  Leu Lys Trp Val Ala  Tyr Gly Phe
    1250             1255             1260

Lys Lys  Tyr Phe Thr Asn Ala  Trp Cys Trp Leu Asp  Phe Leu Ile
    1265             1270             1275

Val Asp  Val Ser Leu Val Ser  Leu Val Ala Asn Thr  Leu Gly Phe
    1280             1285             1290

Ala Glu  Met Gly Pro Ile Lys  Ser Leu Arg Thr Leu  Arg Ala Leu
    1295             1300             1305

Arg Pro  Leu Arg Ala Leu Ser  Arg Phe Glu Gly Met  Arg Val Val
    1310             1315             1320

Val Asn  Ala Leu Val Gly Ala  Ile Pro Ser Ile Met  Asn Val Leu
    1325             1330             1335

Leu Val  Cys Leu Ile Phe Trp  Leu Ile Phe Ser Ile  Met Gly Val
    1340             1345             1350

Asn Leu  Phe Ala Gly Lys Phe  Gly Arg Cys Ile Asn  Gln Thr Glu
    1355             1360             1365

Gly Asp  Leu Pro Leu Asn Tyr  Thr Ile Val Asn Asn  Lys Ser Gln
    1370             1375             1380

Cys Glu  Ser Leu Asn Leu Thr  Gly Glu Leu Tyr Trp  Thr Lys Val
    1385             1390             1395

Lys Val  Asn Phe Asp Asn Val  Gly Ala Gly Tyr Leu  Ala Leu Leu
    1400             1405             1410

Gln Val  Ala Thr Phe Lys Gly  Trp Met Asp Ile Met  Tyr Ala Ala
    1415             1420             1425

Val Asp  Ser Arg Gly Tyr Glu  Glu Gln Pro Gln Trp  Glu Tyr Asn
    1430             1435             1440

Leu Tyr  Met Tyr Ile Tyr Phe  Val Ile Phe Ile Ile  Phe Gly Ser
    1445             1450             1455

Phe Phe  Thr Leu Asn Leu Phe  Ile Gly Val Ile Ile  Asp Asn Phe
    1460             1465             1470

Asn Gln  Gln Lys Lys Lys Leu  Gly Gly Gln Asp Ile  Phe Met Thr
    1475             1480             1485

Glu Glu  Gln Lys Lys Tyr Tyr  Asn Ala Met Lys Lys  Leu Gly Ser
```

-continued

|      |      |      |      |      |      |      |      |      |      |      |      |      |
|------|------|------|------|------|------|------|------|------|------|------|------|------|
| 1490 | | | | 1495 | | | | 1500 | | | | |

Lys Lys Pro Gln Lys Pro Ile Pro Arg Pro Leu Asn Lys Tyr Gln
    1505            1510            1515

Gly Phe Ile Phe Asp Ile Val Thr Lys Gln Ala Phe Asp Val Thr
    1520            1525            1530

Ile Met Phe Leu Ile Cys Leu Asn Met Val Thr Met Met Val Glu
    1535            1540            1545

Thr Asp Asp Gln Ser Pro Glu Lys Ile Asn Ile Leu Ala Lys Ile
    1550            1555            1560

Asn Leu Leu Phe Val Ala Ile Phe Thr Gly Glu Cys Ile Val Lys
    1565            1570            1575

Leu Ala Ala Leu Arg His Tyr Tyr Phe Thr Asn Ser Trp Asn Ile
    1580            1585            1590

Phe Asp Phe Val Val Val Ile Leu Ser Ile Val Gly Thr Val Leu
    1595            1600            1605

Ser Asp Ile Ile Gln Lys Tyr Phe Phe Ser Pro Thr Leu Phe Arg
    1610            1615            1620

Val Ile Arg Leu Ala Arg Ile Gly Arg Ile Leu Arg Leu Ile Arg
    1625            1630            1635

Gly Ala Lys Gly Ile Arg Thr Leu Leu Phe Ala Leu Met Met Ser
    1640            1645            1650

Leu Pro Ala Leu Phe Asn Ile Gly Leu Leu Leu Phe Leu Val Met
    1655            1660            1665

Phe Ile Tyr Ser Ile Phe Gly Met Ala Asn Phe Ala Tyr Val Lys
    1670            1675            1680

Trp Glu Ala Gly Ile Asp Asp Met Phe Asn Phe Gln Thr Phe Ala
    1685            1690            1695

Asn Ser Met Leu Cys Leu Phe Gln Ile Thr Thr Ser Ala Gly Trp
    1700            1705            1710

Asp Gly Leu Leu Ser Pro Ile Leu Asn Thr Gly Pro Pro Tyr Cys
    1715            1720            1725

Asp Pro Thr Leu Pro Asn Ser Asn Gly Ser Arg Gly Asp Cys Gly
    1730            1735            1740

Ser Pro Ala Val Gly Ile Leu Phe Phe Thr Thr Tyr Ile Ile Ile
    1745            1750            1755

Ser Phe Leu Ile Val Val Asn Met Tyr Ile Ala Ile Ile Leu Glu
    1760            1765            1770

Asn Phe Ser Val Ala Thr Glu Glu Ser Thr Glu Pro Leu Ser Glu
    1775            1780            1785

Asp Asp Phe Asp Met Phe Tyr Glu Ile Trp Glu Lys Phe Asp Pro
    1790            1795            1800

Glu Ala Thr Gln Phe Ile Glu Tyr Ser Val Leu Ser Asp Phe Ala
    1805            1810            1815

Asp Ala Leu Ser Glu Pro Leu Arg Ile Ala Lys Pro Asn Gln Ile
    1820            1825            1830

Ser Leu Ile Asn Met Asp Leu Pro Met Val Ser Gly Asp Arg Ile
    1835            1840            1845

His Cys Met Asp Ile Leu Phe Ala Phe Thr Lys Arg Val Leu Gly
    1850            1855            1860

Glu Ser Gly Glu Met Asp Ala Leu Lys Ile Gln Met Glu Glu Lys
    1865            1870            1875

Phe Met Ala Ala Asn Pro Ser Lys Ile Ser Tyr Glu Pro Ile Thr
    1880            1885            1890

```
Thr Thr  Leu Arg Arg Lys His  Glu Glu Val Ser Ala  Met Val Ile
    1895             1900             1905

Gln Arg  Ala Phe Arg Arg His  Leu Leu Gln Arg Ser  Leu Lys His
    1910             1915             1920

Ala Ser  Phe Leu Phe Arg Gln  Gln Ala Gly Ser Gly  Leu Ser Glu
    1925             1930             1935

Glu Asp  Ala Pro Glu Arg Glu  Gly Leu Ile Ala Tyr  Val Met Ser
    1940             1945             1950

Glu Asn  Phe Ser Arg Pro Leu  Gly Pro Pro Ser Ser  Ser Ser Ile
    1955             1960             1965

Ser Ser  Thr Ser Phe Pro Pro  Ser Tyr Asp Ser Val  Thr Arg Ala
    1970             1975             1980

Thr Ser  Asp Asn Leu Gln Val  Arg Gly Ser Asp Tyr  Ser His Ser
    1985             1990             1995

Glu Asp  Leu Ala Asp Phe Pro  Pro Ser Pro Asp Arg  Asp Arg Glu
    2000             2005             2010

Ser Ile  Val
    2015

<210> SEQ ID NO 3
<211> LENGTH: 30
<212> TYPE: PRT
<213> ORGANISM: Homo sapiens

<400> SEQUENCE: 3

Tyr Val Ser Glu Asn Ile Lys Leu Gly Asn Leu Ser Ala Leu Arg Thr
1               5                   10                  15

Phe Arg Val Leu Arg Ala Leu Lys Thr Ile Ser Val Ile Pro
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Consensus sequence of Homo sapiens variants
<220> FEATURE:
<221> NAME/KEY: VARIANT
<222> LOCATION: (7)..(7)
<223> OTHER INFORMATION: X is K or D

<400> SEQUENCE: 4

Tyr Val Thr Glu Phe Val Xaa Leu Gly Asn Val Ser Ala Leu Arg Thr
1               5                   10                  15

Phe Arg Val Leu Arg Ala Leu Lys Thr Ile Ser Val Ile Pro
            20                  25                  30

<210> SEQ ID NO 5
<211> LENGTH: 15
<212> TYPE: PRT
<213> ORGANISM: Artificial Sequence
<220> FEATURE:
<223> OTHER INFORMATION: NESO peptide sequence
<220> FEATURE:
<221> NAME/KEY: MOD_RES
<222> LOCATION: (15)..(15)
<223> OTHER INFORMATION: AMIDATION

<400> SEQUENCE: 5

Val Ser Glu Asn Ile Lys Leu Gly Asn Leu Ser Ala Leu Arg Cys
1               5                   10                  15
```

```
<210> SEQ ID NO 6
<211> LENGTH: 22
<212> TYPE: DNA
<213> ORGANISM: Artificial Sequence
<220> FEATURE:
<223> OTHER INFORMATION: Primer sequence

<400> SEQUENCE: 6
caggttactc tgaaagwgts tg                                                22

<210> SEQ ID NO 7
<211> LENGTH: 36
<212> TYPE: DNA
<213> ORGANISM: Artificial Sequence
<220> FEATURE:
<223> OTHER INFORMATION: Primer sequence

<400> SEQUENCE: 7
ggaagatcta tagacagatg ggggtgtcgt tttggc                                 36

<210> SEQ ID NO 8
<211> LENGTH: 24
<212> TYPE: DNA
<213> ORGANISM: Artificial Sequence
<220> FEATURE:
<223> OTHER INFORMATION: Primer sequence

<400> SEQUENCE: 8
gayattgtgm tsacmcarwc tmca                                              24

<210> SEQ ID NO 9
<211> LENGTH: 21
<212> TYPE: DNA
<213> ORGANISM: Artificial Sequence
<220> FEATURE:
<223> OTHER INFORMATION: Primer sequence

<400> SEQUENCE: 9
ggatacagtt ggtgcagcat c                                                 21

<210> SEQ ID NO 10
<211> LENGTH: 357
<212> TYPE: DNA
<213> ORGANISM: Mus musculus

<400> SEQUENCE: 10
caggttactc tgaaagtgtc tggccctggg atattgcagc cctcccagac cctcagtctg       60
acctgttctt tttctgggtt ttcactgacc acttctggta tgggtgtgag ctggattcgt      120
caggctgcag gaaagggtct ggagtggctg gcacacattt actgggatga tgacaagcgc      180
tataacccag ccctgaagag ccggctcaca atctccaagg atacctccag caaccaagta      240
ttcctcaaca tcaccagtgt ggacactgca gatactgcca catactactg tgctcgaagg      300
gaggactatg ttacgagttt gctaagtggg gccaagggac tctggtcact gtgtttg        357

<210> SEQ ID NO 11
<211> LENGTH: 330
<212> TYPE: DNA
<213> ORGANISM: Mus musculus

<400> SEQUENCE: 11
gatattgtgc tgacccagtc tcctgcttcc ttagctgtat ctctggggca gagggccagc       60
atctcataca gggccagcaa aagtgtcagt acatctggct atagttatat gcactggaac      120
```

-continued

```
cgacagaagc caggacagcc acccagactc ctcatctatc ttgtatccaa cctagaatct      180
ggggtccctg ccaggttcag tggcagtggg tctgggacag acttcaccct caacatccat      240
cctgtggagg aggaggatgc tgcaacctat tactgtcagc acattaggga gcttacacgt      300 tcggagggggg gaccaagctg gaaatacgac                                        330
```

<210> SEQ ID NO 12
<211> LENGTH: 119
<212> TYPE: PRT
<213> ORGANISM: Mus musculus

<400> SEQUENCE: 12

```
Gln Val Thr Leu Lys Val Ser Gly Pro Gly Ile Leu Gln Pro Ser Gln
1               5                   10                  15

Thr Leu Ser Leu Thr Cys Ser Phe Ser Gly Phe Ser Leu Thr Thr Ser
            20                  25                  30

Gly Met Gly Val Ser Trp Ile Arg Gln Ala Ala Gly Lys Gly Leu Glu
        35                  40                  45

Trp Leu Ala His Ile Tyr Trp Asp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Asn Ile Thr Ser Val Asp Thr Ala Asp Thr Ala Thr Tyr Tyr
                85                  90                  95

Cys Ala Arg Arg Glu Asp Tyr Val Thr Ser Leu Leu Ser Gly Ala Lys
            100                 105                 110

Gly Leu Trp Ser Leu Cys Leu
        115
```

<210> SEQ ID NO 13
<211> LENGTH: 110
<212> TYPE: PRT
<213> ORGANISM: Mus musculus

<400> SEQUENCE: 13

```
Asp Ile Val Leu Thr Gln Ser Pro Ala Ser Leu Ala Val Ser Leu Gly
1               5                   10                  15

Gln Arg Ala Ser Ile Ser Tyr Arg Ala Ser Lys Ser Val Ser Thr Ser
            20                  25                  30

Gly Tyr Ser Tyr Met His Trp Asn Arg Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Tyr Asp
            100                 105                 110
```

<210> SEQ ID NO 14
<211> LENGTH: 7
<212> TYPE: PRT
<213> ORGANISM: Mus musculus

<400> SEQUENCE: 14

```
Gly Phe Ser Leu Thr Thr Ser
```

-continued

```
1                   5

<210> SEQ ID NO 15
<211> LENGTH: 5
<212> TYPE: PRT
<213> ORGANISM: Mus musculus

<400> SEQUENCE: 15

Tyr Trp Asp Asp Asp
1                   5

<210> SEQ ID NO 16
<211> LENGTH: 9
<212> TYPE: PRT
<213> ORGANISM: Mus musculus

<400> SEQUENCE: 16

Arg Glu Asp Tyr Val Thr Ser Leu Leu
1                   5

<210> SEQ ID NO 17
<211> LENGTH: 15
<212> TYPE: PRT
<213> ORGANISM: Mus musculus

<400> SEQUENCE: 17

Arg Ala Ser Lys Ser Val Ser Thr Ser Gly Tyr Ser Tyr Met His
1                   5                   10                  15

<210> SEQ ID NO 18
<211> LENGTH: 7
<212> TYPE: PRT
<213> ORGANISM: Mus musculus

<400> SEQUENCE: 18

Leu Val Ser Asn Leu Glu Ser
1                   5

<210> SEQ ID NO 19
<211> LENGTH: 10
<212> TYPE: PRT
<213> ORGANISM: Mus musculus

<400> SEQUENCE: 19

Gln His Ile Arg Glu Leu Thr Arg Ser Glu
1                   5                   10
```

MONOCLONAL ANTIBODIES AGAINST NEONATAL Na$_v$1.5

CROSS-REFERENCE TO RELATED APPLICATIONS

This application is a national stage filing under 35 U.S.C. 371 of PCT/EP2021/051317, filed Jan. 21, 2021, which was published by the International Bureau in English on Jul. 29, 2021, and which claims priority from European Application No. 20152789.2, filed Jan. 21, 2020, each of which is hereby incorporated in its entirety by reference in this application.

FIELD OF THE INVENTION

The present invention relates to the field of cancer therapy. In particular, the present invention relates to the field of treatment of metastasizing cancers and to therapeutic means and methods.

BACKGROUND OF THE INVENTION

Several major human carcinomas express functional voltage-gated Na$^+$ channels (VGSCs) which promote their cellular invasiveness in vitro and metastasis in vivo (Djamgoz et al., 2019). In humans, there are nine different VGSC alpha subunits or "Nav" proteins (Nav1.1 to Nav1.9), encoded by the genes SCN1A, SCN2A, SCN3A, SCN4A, SCN5A, SCN8A, SCN9A, SCN10A and SCN11A, respectively. The alpha subunit of VGSCs is a transmembrane protein with 4 repetitive transmembrane domains (termed DI, DII, DIII and DIV), which each contains 6 transmembrane spanning sections that are termed S1-S6. Na$^+$ ions flow through a pore formed by S5 and S6 combined from all 4 domains. The S4 segment plays a central role in voltage sensing and channel activation. The smaller beta subunits contain an N-terminal extracellular immunoglobulin (Ig) loop, a transmembrane domain and an intracellular domain, and function as regulatory and adhesion molecules.

Human Nav1.5 is encoded by the gene SCN5A, a highly conserved gene located on human chromosome 3, where it spans more than 100 kb. The gene consists of 28 exons, of which exon 1 and in part exon 2 form the 5' untranslated region (5'UTR), and exon 28 forms the 3' untranslated region (3'UTR) of the RNA. More than 10 different splice isoforms have been described for SCN5A, of which several harbour different functional properties. Importantly, Nav1.5 is developmentally regulated via alternative splicing of exon 6, giving rise to 'adult' and 'neonatal' or 'foetal' variants of the Nav1.5 protein that differ in the S3-S4 region of DI by several amino acids. The foetal and adult form of the protein can have 7 amino acid differences in the DI:S3-S4 region of the channel protein.

It has previously been found that the foetal/neonatal isoform of Na$_v$1.5 (nNa$_v$1.5) is associated with metastatic cancers and in vitro data have demonstrated that it is possible to interfere with the metastatic ability of malignant cells by blocking nNa$_v$1.5 (Djamgoz et al., 2019).

Chioni et al. (2005) describes the generation of an anti-peptide polyclonal antibody, named NESOpAb, which specifically recognised 'neonatal' but not 'adult' Na$_v$1.5 when tested on cells specifically over-expressing one or other of these Na$_v$1.5 spliced forms.

However, there is still a need for therapeutic and diagnostic means and methods for cancers, particularly cancers associated with nNa$_v$1.5 expression.

It is an object of embodiments of the invention to provide such therapeutic and diagnostic means and methods.

SUMMARY OF THE INVENTION

The present inventor has identified monoclonal antibodies which specifically bind to nNa$_v$1.5.

So, in one aspect, the present invention provides a monoclonal antibody, or an antigen-binding fragment thereof, which specifically binds to neonatal 5'-exon splice variants of the a subunit of Na$_v$1.5 (nNa$_v$1.5), optionally comprising human constant heavy (CH) and constant light (CL) domains and/or human framework (FR) regions.

In one aspect, the present invention provides a chimeric antigen receptor (CAR) which specifically binds to neonatal 5'-exon splice variants of the a subunit of Na$_v$1.5 (nNa$_v$1.5), optionally comprising an antigen-binding fragment derived from the monoclonal antibody of the preceding aspect.

These and other aspects and embodiments of the invention are disclosed in more detail below.

LEGENDS TO THE FIGURES

Figure 3:
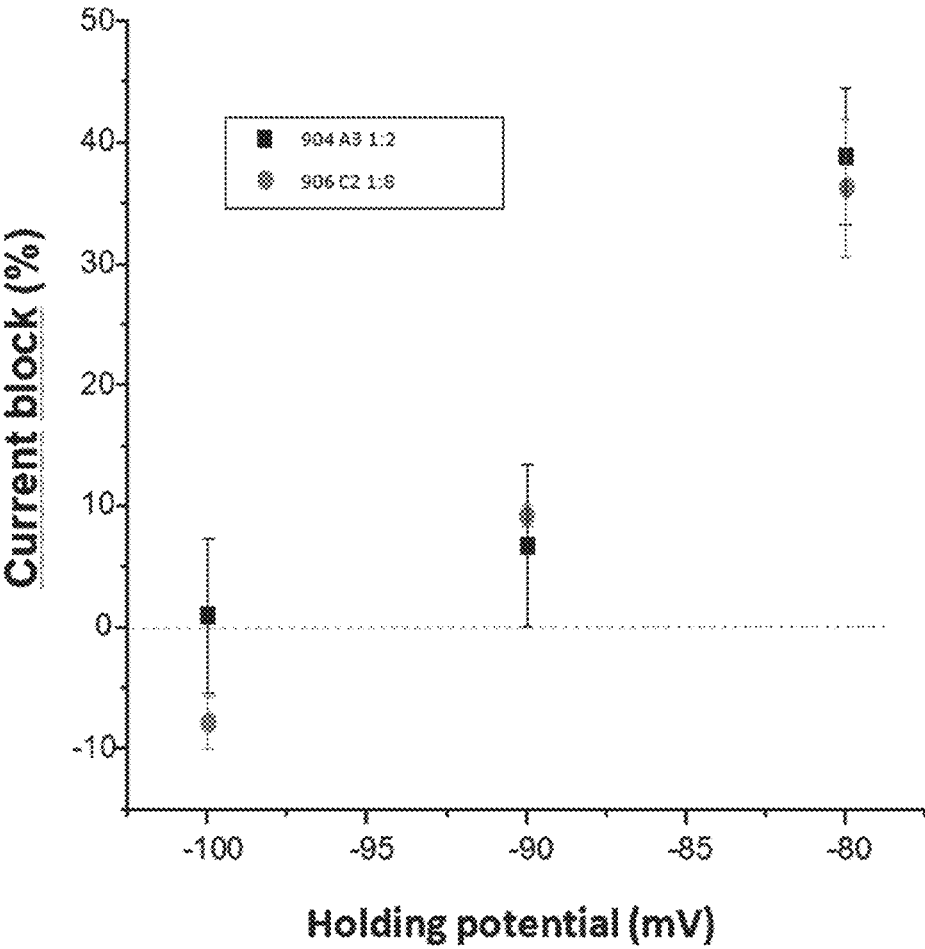

FIG. 3 shows the results of patch-clamp recordings performed on EBNA cells stably expressing neonatal Nav1.5 as previously described by Chioni et al. (2005). The blocking ability of mAb candidates (supernatants) was tested by short-term application using a 'puff' pipette whilst clamping the cells at different holding potentials. The figure shows the dose dependent blockage of nNa$_v$1.5 currents by the A3 and C2 mAbs. Each data point denotes means+/− standard error (n=4-6). The dotted horizontal line denotes 'null effect' for ease of comparison.

FIG. 4 shows the VH (A) and VL (B) amino acid sequences of the A3 antibody (SEQ ID NO: 12 and 13, respectively), with the amino acid positions numbered and the CDR residues (shaded amino acid positions) defined according to the Kabat numbering system, as described elsewhere herein.

DETAILED DISCLOSURE OF THE INVENTION

Cells expressing neonatal splice forms of the α chain of Na$_v$1.5 (in the following collectively termed nNa$_v$1.5) are exclusively or almost exclusively found in metastatic cancer tissues. For instance, no expression was found in healthy colon, small intestine, stomach, prostate, brain, skeletal muscle, and cardiac muscle. This finding demonstrates that therapeutic approaches that target this particular protein will target a tumour specific antigen. In turn this means that targeting of this particular antigen is highly likely to be clinically safe due to the low abundancy/absence of the antigen in normal tissue. nNa$_v$1.5 has also been found to be strongly expressed by human colon polyps, consistent with their pre-cancerous nature.

It has also been found that a polyclonal antibody (NESOpAb) blocks nNa$_v$1.5 current with two orders of magnitude higher affinity compared with the currents generated by (i) the closest related protein, adult Na$_v$1.5 (aNav1.5) and (ii) Na$_v$1.7. Further, the binding of the antibody is use dependent, i.e. blockage of nNa$_v$1.5 by NESOpAb is much more efficient when the channel is opening and closing rather than when it is just closed. Moreover, the binding of the NESOpAb antibody is voltage dependent, meaning that the binding becomes more effective as the membrane potential is depolarized. This latter characteristic renders a nNa$_v$1.5 specific antibody even more specific to cancer cells, which are well known to have depolarized resting potentials.

The binding of the antibody also leads to hyperpolarization of nNa$_v$1.5 "availability", making channel activation less likely.

Lysine (K) at position 211 in the middle of the spliced region of nNa$_v$1.5 has been found to be critical for the binding of NESOpAb. Mutating it back to aspartate (D) as in the adult (double-charge change), reduced blocking efficacy to the level of aNav1.5.

As described in Example 1, monoclonal antibodies binding to nNav1.5 have now been identified. A monoclonal antibody according to the present invention can be defined by its binding specificity, particularly by its specific binding to neonatal 5'-exon splice variants of the α subunit of nNa$_v$1.5. Typically, the monoclonal antibody binds more readily to a nNav1.5 (e.g., a nNa$_v$1.5 comprising the amino acid sequence of residues 206 to 219 of SEQ ID NO:2) than to an adult 3'-exon splice variant of the α subunit of Nav1.5 (aNav1.5) (e.g., comprising the amino acid sequence of residues 206 to 219 of SEQ ID NO: 1), such as, for example, with a factor of at least 1.5:1, at least 2:1, at least 3:1, at least 4:1, at least 5:1, at least 10:1 or at least 20:1, to the nNa$_v$1.5 as compared to the aNav1.5 (nNav1.5:aNav1.5). The monoclonal antibody may also or alternatively bind nNa$_v$1.5 with at least 2 times, such as at least 3 times, such as at least 4 times, such as at least 5 times, such as at least 10 times, such as at least 20 times, such as at least 100 times higher binding affinity compared to binding to adult 3'-exon splice variants of the α subunit of adult Nav1.5 (aNav1.5). For example, the monoclonal antibody may bind nNa$_v$1.5 comprising SEQ ID NO:2 with a K$_D$ at most about half, such as at most about one third, such as at most about one fourth, such as at most about one fifth, such as at most about one tenth, such as at most about one twentieth, such as at most one hundredth, of that of its binding to adult 3'-exon splice variants of the α subunit of Na$_v$1.5 (aNav1.5) comprising SEQ ID NO:1.

In one embodiment, the nNav1.5 to which the monoclonal antibody binds comprises an amino acid sequence that differs from SEQ ID NO:1 in at least amino acid residue 211, such as in amino acid residues 206, 207, 209, 210, 211, 215, and 234. For example, the nNav1.5 may comprise amino acid residues V, S, N, I, K, L, and P in positions 206, 207, 209, 210, 211, 215, and 234 respectively, where aNav1.5 comprises the amino acid residues T, T, F, V, D, V, and S in the same/corresponding positions. In a specific embodiment, the nNav1.5 is human nNav1.5. In another specific embodiment, the monoclonal antibody binds to an epitope in nNav1.5, which has the residue Lys (K) in position 211. In some embodiments, the monoclonal antibody binds to a nNav1.5 comprising the peptide segment VSENIKLGNL-SALR, corresponding to residues 206 to 219 of SEQ ID NO:2. In one specific embodiment, the monoclonal antibody binds to SEQ ID NO:5 (herein referred to as "NESO peptide").

The monoclonal antibody may also be characterized by comprising human sequences, e.g., human CH and CL domains. In some embodiments, all constant domains, framework regions, or constant and framework regions of the monoclonal antibody, are human. In certain embodiments, the monoclonal antibody is a chimeric antibody, a humanized antibody or a fully human antibody. Antigen-binding fragments (Fab) of such a monoclonal antibody, including Fab$_2$-fragments, Fab' fragments and single-chain Fv (scFv) fragments, are also provided. A scFv typically comprises the variable portions of an immunoglobulin heavy and light chain, fused by a flexible linker.

Chimeric antigen receptors (CARs), artificial T cell receptors which are also known as chimeric T cell receptors and/or chimeric immunoreceptors, are engineered receptors, which graft a selected specificity onto an immune effector cell. These receptors may, for example, be used to graft the specificity of a monoclonal antibody onto a T cell or Natural Killer (NK) cell, using, e.g., retroviral vectors to transduce the cells with coding sequences. Such cells are under investigation as a therapy for cancer, using a technique called adoptive cell transfer. Briefly, T cells are removed from a patient and modified so that they express a CAR specific to the patient's particular cancer. Upon reintroduction into the patient, the T cells can then recognize and kill the cancer cells. The design, construction and therapeutic use of CARs have been reviewed by, e.g., Dotti et al. (2014) and Sadelain et al. (2013).

As set forth herein, the CARs of the present invention comprise a binding portion which specifically binds to neonatal 5'-exon splice variants of the α subunit of Nav1.5 (nNav1.5), a transmembrane domain and an endodomain.

The binding portion may advantageously comprise an antigen-binding portion of a monoclonal antibody, such as an antigen-binding fragment, which specifically binds to neonatal 5'-exon splice variants of the α subunit of nNav1.5. Preferably, the antigen-binding fragment is an antigen-binding fragment of a monoclonal antibody according to an aspect or embodiment described herein. Suitable formats of antigen-binding fragments include, without limitation, Fab-fragments and scFv fragments. The scFv may also include an N-terminal signal peptide to direct the nascent protein to the endoplasmic reticulum and subsequent surface expression.

The transmembrane domain is typically a hydrophobic alpha helix derived from the original molecule of the endodomain that protrudes into the cell and transmits the desired signal. In embodiments where the endodomain comprises two or more portions that are derived from different molecules as described below, the transmembrane portion typically derives from the same molecule as the most membrane-proximal portion of the endodomain.

The domains of the CAR may be fused directly to each other or may be joined by peptide linkers. For example, the binding domain, e.g., the scFv, may be fused to the transmembrane domain via a peptide linker, typically a flexible peptide allowing the binding domain to orient in different directions to enable binding to the nNav1.5 antigen. In some embodiments, the peptide linker joining a binding portion which is an antigen-binding fragment and the transmembrane domain may comprise the hinge portion of the constant region of an immunoglobulin, such as IgG1 or IgG4.

The endodomain is the signalling portion of the CAR construct, sending an activation signal to the T or NK cell upon binding of the binding portion to the antigen. Typically, the endodomain comprises a signalling domain derived from a T cell receptor molecule, preferably CD3-ζ (CD3-zeta) which contains immunoreceptor tyrosine-based activation motifs (ITAMs) transmitting an activation signal. In some embodiments, the endodomain further comprises one or more costimulatory molecules, typically at least one of CD27, CD28, 4-IBB and OX40, to enhance the activation signal.

In some embodiments, the different portions of the CAR construct are arranged, from N- to C-terminus, as follows: nNa$_v$1.5-binding domain/hinge/transmembrane domain/endodomain, wherein the nNa$_v$1.5-binding domain may be a scFv, the hinge may comprise an IgG1 or IgG4 hinge region, and the transmembrane domain and the most membrane-proximal molecule of the endodomain may derive from the same molecule. The endodomain may, for example, comprise, from membrane-proximal to membrane-distal, CD3-zeta, CD28/CD3-zeta, CD28/4-IBB/CD3-zeta.

An exemplary CAR vector, such as a retroviral vector which includes a nucleic acid encoding a CAR, can be transfected into T cells and/or NK cells. In some embodiments, the T cells are CD8+ T cells. In some embodiments, the T cells are CD4+ T cells.

Definitions

It is to be understood that this invention is not limited to particular aspects and embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, technical and scientific terms used herein have the same meaning as commonly understood by one of ordinary skill in the art to which this invention belongs.

A "Na$_v$1.5" denotes the α unit of a voltage gated sodium channel (VGSC), where nNa$_v$1.5 is the "neonatal form" (Chioni et al., 2005; Fraser et al., 2005; UniprotKB Q14524 (SCN5A_HUMAN)). The amino acid sequence of the α subunit of Na$_v$1.5 is set forth herein as SEQ ID NO:1 (UniProt Q14524-1).

As used herein, "neonatal Nav1.5" (nNav1.5), also referred to herein as "foetal Nav1.5" or "fetal Nav1.5", comprises an a subunit amino acid sequence that differs from SEQ ID NO:1 in at least amino acid residue 211, such as in amino acid residues 206, 207, 209, 210, 211, 215, and 234. Preferably, in nNav1.5, the amino acid at position 211 of SEQ ID NO:1 is K (Lys). For example, the nNav1.5 may comprise amino acid residues V, S, N, I, K, L, and P in positions 206, 207, 209, 210, 211, 215, and 234 respectively, where aNav1.5 comprises the amino acid residues T, T, F, V, D, V, and S in the same/corresponding positions. In one embodiment, in the neonatal variant, residues 206-211 of SEQ ID NO:1 are changed from TTEFVD→VSENIK, optionally wherein, in the neonatal variant, the amino acid residue at position 215 is changed from V→L and/or the amino acid residue at position 234 is changed from S→P. A specific example of a nNa$_v$1.5 α subunit amino acid sequence is illustrated in SEQ ID NO:2 in the Sequence Table herein (UniProtKB-H9KVD2 (H9KVD2_HUMAN)), where the bold, underlined segment corresponds to (alternatively spliced) exon 6.

As used herein, the term "binding molecule" refers in its broadest sense to a molecule that specifically binds to an antigenic determinant, such as an epitope in nNa$_v$1.5. A binding molecule typically comprises one or more "antigen-binding domains" as described herein. Non-limiting examples of binding molecules include an antibody, a fragment thereof, an antibody-drug conjugate thereof, a bispecific or other multispecific antibody thereof, and a CAR comprising an antigen-binding portion of an antibody, which retain the antigen-specific binding of the antibody.

An "antibody" or "immunoglobulin", used interchangeably herein, includes at least a variable domain of a heavy chain and a variable domain of a light chain, except in the case of a camelid antibody which may only include a variable domain of a heavy chain. The structure of immunoglobulins has been well characterized. See for instance Fundamental Immunology Ch. 7 (Paul, W., ed., 2nd ed. Raven Press, N.Y. (1989)). Unless contradicted by context, the term "antibody" as used herein encompasses any molecule ranging from a small antigen-binding fragment of an antibody to a full-sized antibody, typically including two complete heavy chains and two complete light chains. Heavy chains are classified as gamma, mu, alpha, delta, or epsilon, (γ, μ, α, δ, ε), which in turn determines the "isotype" of the antibody as IgG, IgM, IgA IgG, or IgE, respectively. There are also subclasses among each isotype (e.g., γ1-γ4) or α1-α2). Modified versions of each of these immunoglobulins and their respective subclasses, including both naturally occurring allotypes as well as mutants or fragments modulating properties of interest, are also well known in the art.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are expressed, e.g., by hybridomas, B cells or genetically engineered host cells.

Each heavy chain is typically comprised of a heavy chain variable (VH) region and a heavy chain constant (CH) region. The CH region typically is comprised of three domains, CH1, CH2, and CH3. The heavy chains are typically inter-connected via disulfide bonds in the so-called "hinge region". Each light chain is typically comprised of a light chain variable (VL) region and a light chain constant region, the latter typically comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL region is typically composed of three CDRs and four FRs, arranged from amino-terminus to carboxy-terminus in the following order: FR1, CDR1, FR2, CDR2, FR3, CDR3, FR4. The FRs act to form a scaffold that provides for positioning the CDRs in correct orientation by inter-chain, non-covalent interactions, whereas the binding domain formed by the positioned CDRs defines a surface complementary to the epitope on the immunoreactive antigen. This complementary surface promotes the non-covalent binding of the antibody to its cognate epitope.

The amino acids that make up the CDRs and the FRs, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.,* 196:901-917 (1987), which are incorporated herein by reference in their entireties). Application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody. Unless use of the Kabat numbering system is explicitly noted, however, consecutive numbering is used for all amino acid sequences in this disclosure.

TABLE 1

| CDR Definitions* | | |
| --- | --- | --- |
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al.

Various forms of antigen-binding fragments of antibodies are well-known in the art, and include, e.g., Fab, Fab' and F(ab')$_2$, Fd, Fvs, single-chain Fvs (scFv), single-chain antibodies and disulfide-linked Fvs (sdFv). ScFv molecules are known in the art and are described, e.g., in U.S. Pat. No. 5,892,019.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. As used herein, an antibody or antigen-binding fragment thereof which "specifically binds to neonatal 5'-exon splice variants of the α subunit of Na$_v$1.5 (nNa$_v$1.5)" typically means that the antibody or antigen-binding fragment binds more readily to a nNa$_v$1.5 than it does to aNav1.5. In some embodiments, the nNa$_v$1.5 comprises the peptide segment VSENIKLGNL-SALR, corresponding to residues 206 to 219 of SEQ ID NO:2; the peptide segment of SEQ ID NO:3, corresponding to exon 6. In some embodiments, the nNa$_v$1.5 comprises SEQ ID NO:2 or at least the extracellular portion of SEQ ID NO:2 that comprises residues 206 to 219. An aNav1.5 may comprise SEQ ID NO:1 or at least the extracellular portion of SEQ ID NO:1 that comprises residues 206 to 219.

An antibody or antigen-binding fragment thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" or "binding affinity" refers to a measure of the strength of the binding of an individual epitope with one or more binding domains, e.g., of an immunoglobulin molecule. See, e.g., Harlow et al., Antibodies: A Laboratory Manual, (Cold Spring Harbor Laboratory Press, 2nd ed. 1988) at pages 27-28. The affinity of an antibody or fragment can often be described or specified in terms of their dissociation constant or K$_D$ in binding to the antigen. The K$_D$ of an antibody specifically binding to an antigen can be, for example, no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10-5$ M, $10-5$ M, $5 \times 10^{-6}$ M, $10^{-6}$ M, $5 \times 10^{-7}$ M, $10^{-7}$ M, $5 \times 10^{-8}$ M, $10^{-8}$ M, or $5 \times 10^{-9}$ M, and can also be for, example, no greater than $10^{-9}$ M, $5 \times 10^{-10}$ M, $10^{-11}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

As used herein, the term "chimeric antibody" usually refers to an antibody in which at least part of the heavy chain constant region of a non-human antibody is replaced by the corresponding heavy chain constant region of a human antibody of a specific isotype.

A "humanized" antibody is an engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein, unless contradicted by context, the terms "monoclonal antibody", "mAb", "monoclonal antibody composition" or the like refer to a preparation of antibody molecules of a single molecular composition. A monoclonal antibody preparation can be generated by a hybridoma, e.g., a B cell obtained from an animal fused to an immortalized cell, or by means of recombinant expression of nucleic acid(s) encoding the antibody in a host cell.

A monoclonal antibody or antigen-binding fragment thereof can be monovalent, bivalent or multivalent, referring to the number of antigen-binding domains in the given molecule (i.e., one, two and more than one, respectively). An antibody in standard IgG format, for example, is bivalent. A bivalent or multivalent binding molecule can be monospecific, i.e., where all of the antigen-binding domains bind to the same epitopes and are typically the same, or can be bispecific or multispecific, e.g., where two or more binding domains bind to different epitopes on the same antigen, or bind to entirely different antigens, because of different antigen-binding domains.

As used herein, the terms "fragment," "variant," "derivative" and "analog" of a reference compound, e.g., a polypeptide, refer to modified versions of that reference compound which retain at least some of the properties of the reference compound. For example, a "fragment" or a "variant" of a reference native antibody or polypeptide which, for example, provides for specific binding to an antigen, typically retains that ability. Variants of, e.g., a polypeptide include fragments as described above, and also polypeptides with altered amino acid sequences due to amino acid substitutions, deletions, or insertions. Variant polypeptides can comprise conservative or non-conservative amino acid substitutions, deletions or additions.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions which do not eliminate antigen-binding are well-known in the art (see, e.g., Brummell et al., Biochem. 32: 1180-1187 (1993); Kobayashi et al., Protein Eng. 12(10): 879-884 (1999); and Burks et al., Proc. Natl. Acad. Sci. USA 94:412-417 (1997)).

As used herein, a sequence that is "similar" to a reference sequence typically has a sequence identity of at least about 80%, such as at least about 85%, such as at least about 90%, such as at least about 95%, such as at least about 96%, 97%, 98% or 99% to the reference sequence; whereas a sequence "identical" to a reference sequence has a sequence identify of 100% to the reference sequence or at least a segment thereof.

The percent identity between two sequences is a function of the number of identical positions shared by the sequences (i.e., % homology=# of identical positions/total # of positions x 100), taking into account the number of gaps, and the length of each gap, necessary for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444 453 (1970) algorithm.

Specific Embodiments of the Invention

Figure 1:
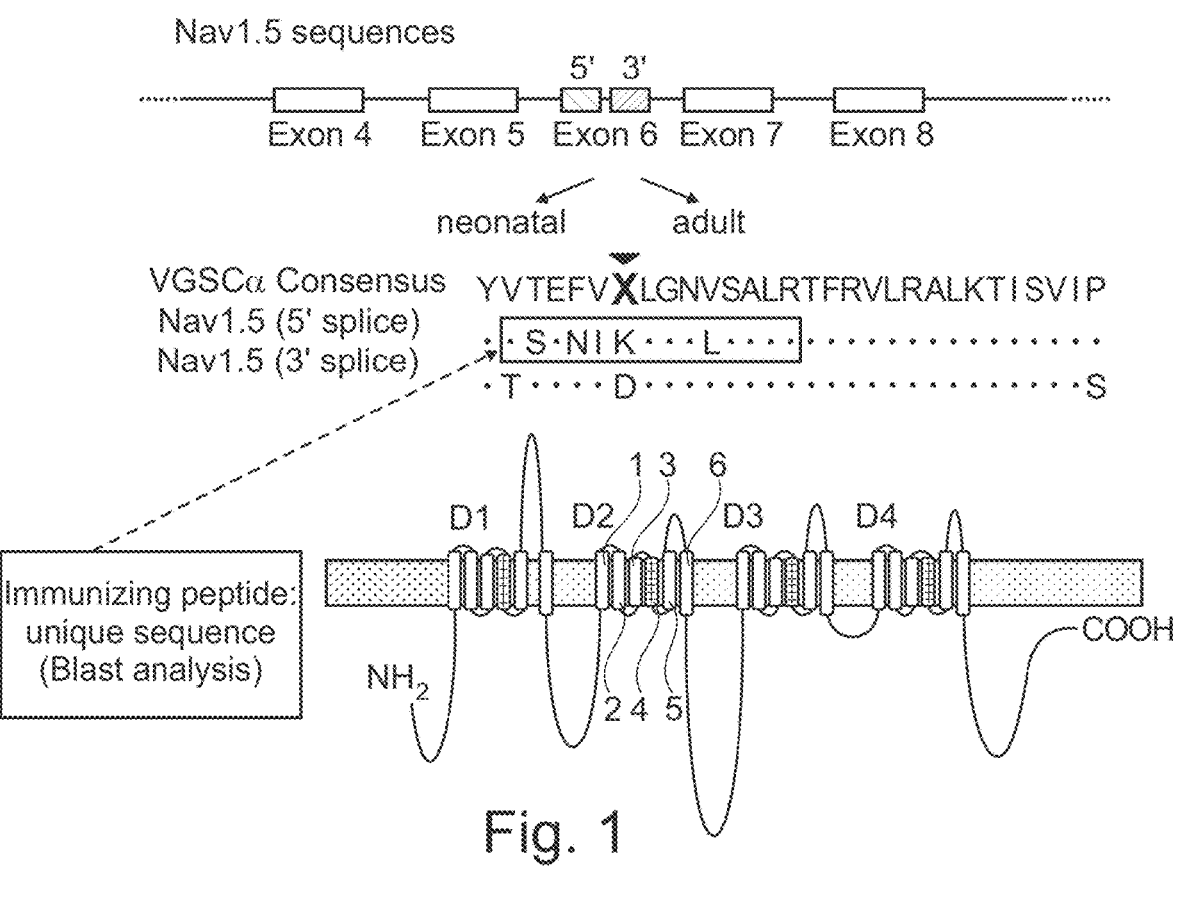
FIG. 1 shows Nav1.5 splice variant sequences encoded by exon 6 of the SCN5A gene and a consensus sequence (SEQ ID NO:4).

As described in Example 1, monoclonal antibodies were raised against the peptide described in Chioni et al., (2005); NH₂-VSENIKLGNLSALRC-amide (SEQ ID NO:5), herein referred to as "NESO peptide" (Chioni et al., 2005) and were found to specifically bind to nNav1.5 (FIG. 1).

The present invention relates to a monoclonal antibody which specifically binds to neonatal 5'-exon splice variants of the α subunit of Na$_v$1.5 (nNa$_v$1.5), to antigen-binding fragments and CARs derived from such monoclonal antibodies as well as to their use in diagnostic and therapeutic methods. These are set out in more detail below, wherein the term "binding molecule of the invention" can refer to any one or more of a monoclonal antibody, antigen-binding fragment thereof, or a CAR (optionally in the form of a T or NK cell comprising the CAR), which specifically binds to nNa$_v$1.5, as described in any aspect or embodiment herein.

Binding Molecules

A binding molecule according any aspect or embodiment comprises a binding domain allowing for specific binding to nNav1.5. Typically, a binding molecule comprises one or more antibody variable domains, such as a VH region and a VL region, comprising VH CDR 1-3 and VL CDR 1-3 forming the binding domain.

In some embodiments, the binding molecule is a monoclonal antibody which specifically binds to nNa$_v$1.5.

In some embodiments, the binding molecule is an antigen-binding fragment of a monoclonal antibody, which specifically binds to nNa$_v$1.5.

In some embodiments, the binding molecule is a CAR (optionally in the form of a T or NK cell comprising the CAR), which specifically binds to nNa$_v$1.5.

In some embodiments, the binding molecule specifically binds to a nNav1.5 comprising the peptide VSENIKLGNL-SALR, corresponding to residues 206 to 219 of SEQ ID NO:2.

In some embodiments, the binding molecule specifically binds to a Nav1.5 comprising YVSENIKLGNLSAL-RTFRVLRALKTISVIP (SEQ ID NO:3), which is the amino acid sequence corresponding to exon 6 of a nNav1.5.

In some embodiments, the binding molecule specifically binds the NESO peptide (SEQ ID NO:5), described in Chioni et al. (2005).

In some embodiments, the binding molecule specifically binds to a nNa$_v$1.5 comprising at least the extracellular portion of SEQ ID NO:2.

Figure 2:
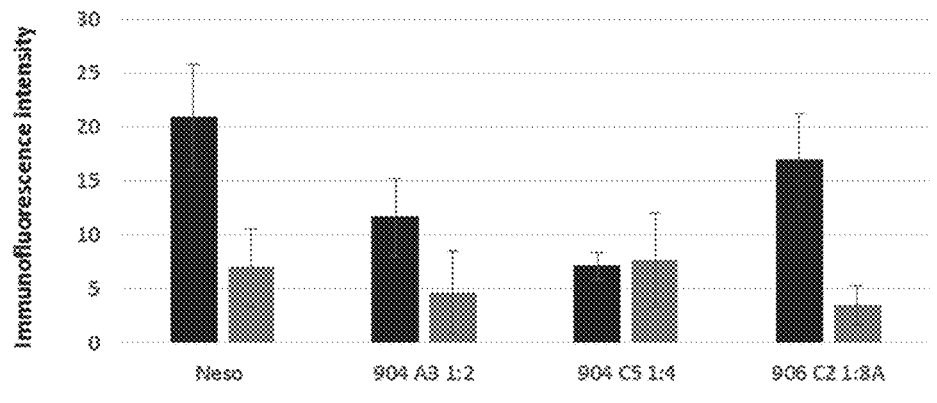
FIG. 2 shows the results of immunocytochemical tests, using mAbs obtained from hybridomas and EBNA cell lines stably expressing nNav1.5 or aNav1.5. See Example 1 for details.

In some embodiments, the binding molecule specifically binds to a cell expressing a nNav1.5 as defined herein, e.g., a Nav1.5 comprising SEQ ID NO:2. The preparation of a nNav1.5 expressing cell line as well as an aNav1.5-expressing control cell line, both prepared by transfecting EBNA-293 cells with DNA encoding nNav1.5 and aNav1.5, respectively, is described in Chioni et al. (2005). These are suitable for evaluating specific binding to nNav1.5 according to standard methods known in the art. See also Example 1 and FIG. 2.

In some embodiments, the binding molecule binds more readily to a first cell or cell preparation expressing a nNav1.5 than to a second cell or cell preparation expressing an aNav1.5, e.g., wherein the cell or cell preparation derives from EBNA-293 cells respectively transfected with DNA encoding a nNav1.5 and an aNav1.5 as described in Chioni et al. (2005) and is incubated with the binding molecule under appropriate conditions. The binding molecule may, for example, be labelled with a detectable molecule, or its binding to the cell detected by a secondary, labelled antibody, so that, after the incubation, it is possible to determine a first signal reflecting the number of binding molecules bound to the first cell or cell preparation and a second signal reflecting the number of binding molecules bound to the second cell or cell preparation. In some embodiments, the ratio between the first and second signal is at least 2:1, such as at least 3:1, such as at least 4:1, such as at least 5:1, such as at least 10:1. Alternatively, the ability of the binding molecule to bind to a nNav1.5 and an aNav1.5 can be determined in an in silico assay where the respective protein is bound to a solid support. Methods for determining the dissociation constant (KD) reflecting the binding affinity of an antibody to an antigen or other protein are well known in the art.

The binding molecule may also be characterized by specific VH, VL and/or CDR amino acid sequences, such as specific VH, VL and CDR amino acid sequences of monoclonal antibodies produced by clones or subclones described in Example 1.

Accordingly, in Certain Embodiments, the Binding Molecule Comprises (a) VH CDRs 1, 2 and 3 and VL CDRs 1, 2 and 3 of clone A3;

(b) VH CDRs 1, 2 and 3 and VL CDRs 1, 2 and 3 of subclone A3-2

(c) VH CDRs 1, 2 and 3 and VL CDRs 1, 2 and 3 of subclone C2-2, or (d) VH and VL domains of clone A3.

In some embodiments, the binding molecule comprises a VH region comprising a complementary-determining region (CDR) 3 comprising SEQ ID NO: 16, or a variant thereof comprising 1, 2 or 3 mutations; and a variable light chain (VL) region comprising a CDR3 comprising SEQ ID NO: 19, or a variant thereof comprising 1, 2 or 3 mutations. The mutations may include, for example, one or more of substitutions, deletions and insertions of amino acids. In some embodiments, one, two or all mutations are amino acid substitutions, such as conservative amino acid substitutions.

In some embodiments, VH region further comprises a CDR1 comprising SEQ ID NO: 14, or a variant thereof comprising 1, 2 or 3 mutations; and a CDR2 comprising SEQ ID NO: 15, or a variant thereof comprising 1, 2 or 3 mutations; and the VL region comprises a CDR1 comprising SEQ ID NO: 17, or a variant thereof comprising 1, 2 or 3 mutations; and a CDR2 comprising SEQ ID NO: 18, or a variant thereof comprising 1, 2 or 3 mutations. The mutations may include, for example, one or more of substitutions, deletions and insertions of amino acids. In some embodiments, one, two or all mutations are amino acid substitutions, such as conservative amino acid substitutions.

In some embodiments, the binding molecule comprises a VH region comprising the CDR1, CDR2 and CDR3 of the VH region encoded by SEQ ID NO: 10 and a VL region comprising the CDR1, CDR2 and CDR3 of the VH region encoded by SEQ ID NO:11.

In some embodiments, the binding molecule comprises a VH region comprising CDR1, CDR2 and CDR3 amino acid sequences comprising SEQ ID NOS: 14, 15 and 16, respectively, and a VH region comprising CDR1, CDR2 and CDR3 amino acid sequences comprising SEQ ID NOS: 17, 18 and 19, respectively.

In some embodiments, the binding molecule comprises a VH region at least 80%, such as at least 90%, 95%, 97%, 98% or 99% identical, to the VH region encoded by SEQ ID NO: 10, and a VL region at least 80%, such as at least 90%, 95%, 97%, 98% or 99% identical, to the VL region encoded by SEQ ID NO:11.

In a specific embodiment, the binding molecule comprises a VH region comprising the amino acid sequence encoded by SEQ ID NO:10 and a VL region comprising the amino acid sequence encoded by SEQ ID NO:11.

In another specific embodiment, the binding molecule comprises a VH region comprising the amino acid sequence of SEQ ID NO: 12 and a VL region comprising the amino acid sequence of SEQ ID NO: 13.

In some embodiments, the binding molecule is an antibody comprising the antigen-binding sequences, particularly the VH and VL region sequences, of antibody (clone) A3 as described in Example 1.

Also provided is a binding molecule, such as a monoclonal antibody, antigen-binding fragment or CAR, which competitively inhibits a reference monoclonal antibody comprising the heavy chain and light chain of any one of clone A3, subclone A3-2 and subclone C2-2, such as the heavy chain and light chain of antibody (clone) A3, from specifically binding to nNa$_v$1.5, e.g., having the amino acid sequence of SEQ ID NO:2. A binding molecule is said to competitively inhibit binding of such a reference antibody to nNav1.5 if its presence reduces the binding of the reference antibody to the nNav1.5. Competitive inhibition may be determined by any method known in the art, for example, competition ELISA assays. A binding molecule may be said to competitively inhibit binding of the reference antibody to a given epitope by at least 90%, at least 80%, at least 70%, at least 60%, or at least 50%.

Further provided is a monoclonal antibody, antigen-binding fragment or CAR which specifically binds to the same epitope on a nNa$_v$1.5 as a monoclonal antibody comprising the heavy chain and light chain of any one of clone A3, subclone A3-2 and subclone C2-2, such as the heavy chain and light chain of antibody (clone) A3. The epitope may, for example, be a conformational epitope comprising at least 1, 2, 3, 4, 5 or more amino acid residues of exon 6 (SEQ ID NO. 3). The epitope may also be a linear epitope comprising at least 5, 6, 7, 8, 9, 10, 11, 12, 13, 14, 15 or more consecutive amino acids of SEQ ID NO:3. Preferably, the linear or conformational epitope in nNav1.5 comprises one, two, three, four, five, six or all of the amino acid residues V, S, N, I, K, L, and P in positions 206, 207, 209, 210, 211, 215, and 234, respectively. In some embodiments, the nNa$_v$1.5 has the amino acid sequence of SEQ ID NO:2. Methods for determining the epitope of an antibody are well-known in the art, and include, for example, X-ray co-crystallography and cryogenic electron microscopy (cryo-EM), array-based oligo-peptide scanning, site-directed mutagenesis mapping (e.g., alanine-scanning), high-throughput shotgun mutagenesis epitope mapping, hydrogen-deuterium exchange (HDX), and cross-linking-coupled mass spectrometry.

Also provided is a chimeric antigen receptor (CAR) comprising a binding portion which specifically binds to nNa$_v$1.5, a transmembrane domain and an endodomain. The binding portion preferably comprises an antigen-binding fragment of a binding molecule, such as a monoclonal antibody, according to any aspect or embodiment herein.

In some embodiments, at least one of the CAR, the monoclonal antibody and the antigen-binding fragment binds nNa$_v$1.5 more readily than it binds to adult 3'-exon splice variants of the α subunit of Na$_v$1.5 (aNav1.5), optionally with at least 100 times higher binding affinity compared to binding to aNav1.5. In one embodiment, the nNa$_v$1.5 comprises an amino acid sequence that differs from SEQ ID NO:1 in at least amino acid residue 211, such as in amino acid residues 206, 207, 209, 210, 211, 215, and 234. In one embodiment, the nNa$_v$1.5 comprises amino acid residues V, S, N, I, K, L, and P in positions 206, 207, 209, 210, 211, 215, and 234 respectively, and where aNav1.5 comprises the amino acid residues T, T, F, V, D, V, and S in the same/corresponding positions. In one embodiment, the nNa$_v$1.5 is human nNa$_v$1.5. In one embodiment, the CAR binds to an epitope in nNa$_v$1.5, which has the residue Lys (K) in position 211.

In some embodiments, there is provided a T cell or NK cell comprising a CAR according to any aspect or embodiment herein. Also provided is a nucleic acid sequence encoding the monoclonal antibody, antigen-binding fragment or CAR of any aspect or embodiment herein, an expression vector comprising the nucleic acid sequence, and a T cell or NK cell comprising said nucleic acid sequence or said expression vector.

In some embodiments, a binding molecule according to any aspect or embodiment herein is neutralizing. A "neutralizing" binding molecule, as used herein, is intended to refer to a binding molecule whose binding to nNav1.5 results in a reduction or inhibition of at least one biological activity of nNav1.5 or associated with nNav1.5. This reduction or inhibition of the biological activity of Nav1.5 can be assessed by measuring one or more indicators of Nav1.5 biological activity by one or more standard in vitro or in vivo assays known in the art.

For example, electrophysiological assays can be used for determining functional nNav1.5 ion conductance, in the case of Chioni et al. (2005) for evaluating the effect of a polyclonal antibody preparation on functional nNav1.5 ion conductance. Accordingly, the patch-clamp recording assay set out on page 91, section 2.8 of Chioni et al. (2005), hereby specifically incorporated by reference, can be used to evaluate whether a binding molecule as described herein is a neutralizing binding molecule. The effect of a binding molecule on the function of Nav1.5 can also be studied using the following electrophysiological assay, with details as described previously (e.g. Laniado et al., 1997; 2001; Fraser et al., 2003; Grimes et al, 1995), using, for example, nNav1.5 expressing EBNA cells prepared as described in Chioni et al. (2005): Patch pipettes (tip resistances, ~5 MΩ) can be filled with a solution designed to block the outward $K^+$ currents; e.g., (in mM): NaCl 5, CsCl 145, $MgCl_2$ 2, $CaCl_2$) 1, HEPES 10 and EGTA 11, adjusted to pH 7.4 with 1 M CsOH. The intracellular free $Ca^{2+}$ concentration can be estimated, e.g., ~15 nM (Laniado et al., 2001). Whole-cell membrane currents can be recorded from cells that appear 'isolated' in culture, e.g., using an Axopatch 200B amplifier (Axon Instruments, CA, USA). Analogue signals can be filtered at 10 kHz using a low-pass Bessel filter, and series resistance errors can be compensated by >90%. Electrophysiological signals may be sampled at 50 kHz and digitized, e.g., using an interface such as Digidata 1200. Data acquisition and analysis of whole-cell currents can then be performed, e.g., using suitable software such as pClamp software (Axon Instruments). A holding potential of –100 mV may be applied. Standard voltage-clamp protocols were used to study the electrophysiological properties of the VGSC currents. All routine recordings can be done after a suitable time of incubation, e.g., at 24 hours after (re)plating and 24 hours of serum starvation (to match the condition of the invasion assays). Conductance-voltage relationships and other relevant parameters for evaluating VGSC currents can then be calculated using equations (I) to (III) below, with further details provided in Onkal et al. (2008):

Conductance-voltage relationships are determined using the equation:

$$G=I/(V-V_{rev}) \tag{I}$$

where G is the conductance; I the current amplitude; V the test pulse; and $V_{rev}$ the theoretical $Na^+$ reversal potential. Normalized curves for voltage dependence of steady-state activation and inactivation are fitted to a Boltzmann function of the form:

$$G=G_{max}/[1-\exp(V_m-V_{1/2})/k] \tag{II}$$

where $G_{max}$ is the maximal conductance; $V_m$ is the membrane voltage; $V_{1/2}$ is the voltage at which the current is half activated/inactivated, and k is the slope factor of voltage sensitivity. For the time course of recovery from inactivation, the data is plotted as a function of recovery time and fitted to the following single exponential equation:

$$I=A \exp(-t/t)+C \tag{III}$$

where I is normalized current, t is time, t is the time constant, A is the amplitude of the normalized current, and C is the asymptote. More details can be found in Onkal et al. (2008).

Typically, a neutralizing binding molecule according to the present invention results in a significant reduction in VGSC current, e.g. peak VGSC current density and/or absolute current, relative to control and/or significantly reduces the proportion of cells demonstrating VGSC currents, e.g., by at least about 10%, 20% or more, such as by at least 30%, 40%, 50%, 60%, 70% or more as compared to a control.

In one particular embodiment, the VGSC comprises a nNav1.5 α subunit, and a neutralizing binding molecule according to the present invention results in a significant reduction in VGSC current, e.g. peak VGSC current density and/or absolute current, relative to control and/or significantly reduces the proportion of cells demonstrating nNav1.5 currents, e.g., by at least about 10%, 20% or more, such as by at least 30%, 40%, 50%, 60%, 70% or more as compared to a control.

In one particular embodiment, and a neutralizing binding molecule according to the present invention results in a reduction in VGSC current, e.g., peak VGSC current density and/or absolute current, of a VGSC comprising a nNav1.5 α subunit which is higher than the corresponding reduction in VGSC current of a VGSC comprising an aNav1.5 α subunit, e.g., by at least about 10%, 20% or more, such as by at least 30%, 40%, 50%, 60%, 70% or more.

Additionally, the neutralizing ability of a binding molecule to reduce the invasiveness of cancer cells can be determined using the assay described by Fraser et al. (2005) and/or Brackenbury et al. (2007), following optimization of the cell number versus the Matrigel concentration. Subsequently, (i) insert filters (with 8 μm pores) can be coated with 50 μl of 0.21 mg/ml Matrigel (BD Biosciences, Bedford, MA, USA); (ii) a chemotactic gradient can be 0.1-10% FBS; and (iii) the cells can be serum-starved for 24 hours and (iv) about $10^5$ cells can be seeded onto each filter. After a suitable period of incubation, such as 48 hours, the insert can be swabbed and then stained with crystal violet. The invaded cells in 12 non-overlapping fields of view can then be counted, e.g., under ×400 magnification. "Invasiveness" can then be calculated as the number of invaded cells normalized to the largest value observed amongst the different treatment conditions in given experimental sets. Typically, a neutralizing binding molecule of the present invention results in a significant reduction of invasiveness, e.g., by at least about 10%, 20% or more, such as by at least 30%, 40%, 50%, 60%, 70% or 80% as compared to a control. This may be observed both under normoxic and hypoxic conditions.

Suitable controls include, for example, the buffer or other solution in which the binding molecule is dissolved and a control binding molecule whose VH and VL regions specifically bind to an irrelevant antigen but the remainder of the control binding molecule is the same as the test binding molecule. For example, in the case of a binding molecule which is a test monoclonal antibody or test antigen-binding fragment, a control monoclonal antibody or antigen-binding fragment specifically binding to an irrelevant antigen but having the same framework and/or constant regions as the test monoclonal antibody or test antigen-binding fragment can be used.

Also contemplated are binding molecules conjugated to cytotoxic agent, radioisotope, chemotherapeutic drug or the like, e.g., in the form of an antibody-drug conjugate (ADC), which delivers a cytotoxic agent or chemotherapeutic drug to nNav1.5-expressing tumor cells by way of the binding specificity of the binding molecule. In some embodiments, an ADC according to the invention is used to target micrometastases. nNav1.5-based ADCs could offer a particular advantage of recognizing and killing micro-metastases, one of the most difficult problems in clinical management of cancer, since they can be "dormant" and thereby difficult to both detect and treat by conventional means. ADCs are often designed such that the cytotoxic payload is inactive when conjugated to the antibody. The cytotoxic payload may be released intracellularly upon internalization of the ADC after binding to the plasma-membrane of cells, or alternatively in response to proteolytic activity in the tumor microenvironment. This can, for example, be accomplished by way of the binding molecule being conjugated to a cytotoxic agent or chemotherapeutic drug via a cleavable linker, which is cleaved by e.g. an intracellular peptidase or protease or upon internalization of the ADC, or by proteolytic enzymes in the tumor microenvironment. Non-limiting examples of cytotoxic agents include, for example, auristatins, maytansinoids, calicheamicins and amatoxins. Further examples include DNA-targeting agents, e.g. DNA alkylators and cross-linkers, such as calicheamicin, duocarmycin, rachelmycin (CC-1065), pyrrolo[2,1-c] [1,4] benzodiazepines (PBDs), and indolinobenzodiazepine (IGN); microtubule-targeting agents, such as duostatin, such as duostatin-3, auristatin, such as monomethylauristatin E (MMAE) and monomethylauristatin F (M MAF), dolastatin, maytansine, /V(2')-deacetyl-/V(2')-(3-marcapto-1-oxopropyl)-maytansine (DM1), and tubulysin; and nucleoside analogs; as well as analogs, derivatives, or prodrugs thereof. Examples of chemotherapeutic drugs include microtubule-targeting agents such as paclitaxel, docetaxel, vinblastine, vincristine, vinorelbine, duostatins, auristatins, maytansinoids, tubulysins, and dolastatin.

Further contemplated is a multispecific, such as a bispecific, antibody which comprises a first binding domain and a second binding domain, wherein the first and second binding domains have different binding specificities. In one embodiment, the first binding domain binds to nNav1.5 and the second binding domain binds to a second antigen which is not nNav1.5. For example, Nav1.5 has been shown to be physically associated with sodium-hydrogen exchanger protein (NHE1) (Brisson et al., 2013). So, in one embodiment, there is provided a multispecific, such as a bispecific, antibody comprising a first binding domain which specifically binds to nNav1.5 according to any aspect or embodiment herein, and a second binding domain which specifically binds to NHE1. The first binding domain may, for example, have the binding specificity of the monoclonal antibody produced by clone A3, subclone A3-2, or subclone C2-2. Preferably, the first binding domain comprises VH and VL regions comprising the CDRs, VH and/or VL region sequences of antibody (clone) A3, as described in Example 1 and the Sequence Table.

In another embodiment there is provided a multispecific antibody, such as a bispecific antibody, wherein a first binding domain binds to nNav1.5 and a second binding domain which specifically binds to the voltage-dependent ion channel Kv 11.1, also known as hERG1 (the "human Ether-b-go-go-Related Gene") and encoded by the gene KCNH2 (Duranti and Arcangeli. *Ion Channel Targeting with Antibodies and Antibody Fragments for Cancer Diagnosis*. Antibodies (Basel). 2019 May 24; 8(2):33).

A bispecific or multispecific antibody may be particularly useful for treating a cancer expressing both nNa$_v$1.5 and NHE1, or both nNa$_v$1.5 and hERG1. In a particular embodiment, the cancer is a breast cancer.

In another embodiment there is provided a multispecific antibody, such as a bispecific antibody, wherein the first and second binding domains specifically bind to different epitopes on nNav1.5. For example, in one embodiment, the first binding domain may have the binding specificity of the monoclonal antibody produced by clone A3 or A3-2, and the second binding domain may have the binding specificity of the monoclonal antibody produced by subclone C2-2, or vice versa. Preferably, the first binding domain comprises VH and VL regions comprising the CDRs, VH and/or VL region sequences of antibody (clone) A3, as described in Example 1.

Production of Binding Molecules

The disclosure further provides polynucleotides, e.g., an isolated, recombinant, and/or non-naturally occurring polynucleotide, comprising a nucleic acid sequence that encodes at least a subunit of the binding molecule specifically binding to nNav1.5 according to any aspect or embodiment herein. By "polypeptide subunit" is meant a portion of a binding molecule, or antigen binding domain that can be independently translated. Examples include, without limitation, an antibody variable domain, e.g., a VH or a VL region, an antibody heavy chain, an antibody light chain, a single-chain Fv (scFv) antibody comprising a VH or a VL region, a CAR comprising such an scFv, and/or any fragment, variant, or derivative thereof.

In certain aspects, the subunit can comprise an IgG (such as an IgG1, IgG2, IgG3 or IgG4), IgA or IgM heavy chain constant region or fragment thereof, and VH region of a binding molecule which specifically binds to nNav1.5. In certain aspects the nucleic acid sequence can encode α subunit comprising a human IgG constant region or fragment thereof fused to the C-terminal end of a VH region, where the VH region comprises the VH CDR1, CDR2, and CDR3 of the VH region of antibody (clone) A3, or a variant thereof comprising 1, 2 or 3 mutations, such as amino acid substitutions. In some embodiments, the nucleic acid sequence encodes α subunit comprising a human IgG constant region or fragment thereof, such as an IgG1 or IgG4 constant region or fragment thereof, fused to the C-terminal of the amino acid sequence encoded by SEQ ID NO: 10, or a variant thereof as described elsewhere herein.

In certain aspects, the subunit can comprise an antibody VL portion of a binding molecule which specifically binds to nNav1.5 as described above. In certain aspects the nucleic acid sequence can encode α subunit comprising a human antibody light chain constant region or fragment thereof fused to the C-terminal end of a VL region, wherein the VL region comprises the VL CDR1, CDR2, and CDR3 of the VL region of antibody (clone) A3, or a variant thereof comprising 1, 2 or 3 mutations, such as amino acid substitutions. In some embodiments, the nucleic acid sequence encodes α subunit comprising a human light chain constant region, e.g., a human kappa or lambda constant light chain region or fragment thereof, fused to the C-terminal of the amino acid sequence encoded by SEQ ID NO: 11, or a variant thereof as described elsewhere herein.

The disclosure further provides a composition comprising two (or more) polynucleotides encoding different subunits, e.g., an antibody heavy and a light chain, respectively, which collectively can encode a binding molecule which specifically binds to nNav1.5 as described above. In certain aspects, the two polynucleotides making up the composition can be situated on a single vector, e.g., an expression vector. Vectors useful for these purposes are known in the art. Such vectors can also comprise enhancer and other sequences needed to achieve expression of the desired chains.

Further provided are cells, e.g., a hybridoma or a host cell, such as, e.g., a prokaryotic or eukaryotic host cell, comprising a polynucleotide or two or more polynucleotides encoding a binding molecule as provided herein, or any subunit thereof, a polynucleotide composition as provided herein, or a vector or two, three, or more vectors that collectively encode a binding molecule as provided herein, or any subunit thereof. The host cell can, for example, be described as a recombinant host cell. In certain aspects a recombinant host cell provided by the disclosure can express a binding molecule which specifically binds to nNav1.5, or a subunit thereof.

To form the antigen binding domains, the variable regions of antibodies that specifically bind to nNav1.5 can be inserted into expression vector templates for antibodies, e.g., human IgG, IgA or IgM antibodies, thereby creating multimeric binding molecules having at least two bivalent binding units. In brief, nucleic acid sequences encoding the heavy and light chain variable domain sequences can be synthesized or amplified from existing molecules, and inserted into vectors in the proper orientation and in frame such that upon expression, the vector will yield a full length heavy or light chain, or a desired fragment thereof. Multiple vectors or single vectors can be used. These vectors are transfected into host cells and the polypeptide chain(s) thereafter expressed and optionally purified.

In a related aspect, the disclosure provides a method of producing a binding molecule specifically binding to nNav1.5 as provided by this disclosure, where the method comprises culturing a host cell as described above and, optionally, recovering the binding molecule.

In some embodiments, particularly when the binding molecule is CAR, a polynucleotide as described herein may further comprise nucleic acid sequences encoding the other regions typically present in a CAR molecule. For example, the polynucleotide may encode a polypeptide comprising nNav1.5-binding domain/hinge/transmembrane domain/endodomain regions, e.g., wherein the nNav1.5-binding domain may be a scFv, the hinge may comprise an IgG1 or IgG4 hinge region, and the transmembrane domain and the most membrane-proximal molecule of the endodomain may derive from the same molecule. The endodomain may, for example, comprise, from membrane-proximal to membrane-distal, CD3-zeta, CD28/CD3-zeta, or CD28/4-IBB/CD3-zeta.

Therapeutic and Diagnostic Methods

A binding molecule according to any aspect or embodiment described herein, a nucleic acid or vector encoding such a binding molecule, or a cell expressing such a binding molecule, may be used as a medicament, e.g., in methods for treatment or amelioration of cancer, in methods for reducing the risk of metastatic cancer, or both.

A binding molecule according to any aspect or embodiment described herein may also be used as a nNav1.5 detection agent in in vivo or in vitro methods, e.g., to detect nNav1.5 expressing tumours, metastases or cancer cells.

In one embodiment, the binding molecule is a monoclonal antibody which specifically binds to $nNa_v1.5$. In one embodiment, the binding molecule is an antigen-binding fragment of a monoclonal antibody which specifically binds to $nNa_v1.5$. In one embodiment, the binding molecule is a CAR which specifically binds to $nNa_v1.5$, optionally wherein the CAR is comprised in an NK or T cell. Depending on the intended use of the binding molecule, the binding molecule can further be, for example, neutralizing, conjugated to a cytotoxic drug (e.g., as an antibody-drug conjugate (ADC)), or labelled with a detectable label.

In one aspect, the method is for treatment or amelioration of metastatic cancer, comprising administering an effective amount of a binding molecule according to the invention to a patient suffering from metastatic cancer.

In one aspect, the method is for reducing the risk of metastatic cancer in a subject, comprising administering an effective amount of a binding molecule according to the invention to said subject.

In one aspect, the method is a method for detecting the presence of metastatic cancer in a subject, the method comprising administering a labelled antibody or antigen-binding fragment thereof, which specifically recognizes $nNa_v1.5$, to the subject and subsequently measuring signal distribution derived from the labelled antibody or antigen-binding fragment in said subject, where a localised dense signal in a part of the body of the subject is indicative of the presence of metastatic disease in said part of the body.

In one aspect, the method is for detecting the presence of nNav1.5 in a biological sample from a subject, the method comprising contacting the biological sample with an antibody or antigen-binding fragment thereof which specifically recognizes $nNa_v1.5$, and subsequently detecting binding of the antibody or antigen-binding fragment to the biological sample.

VGSC is a mammalian gene family. Accordingly, suitable subjects or patients include mammalian subjects or patients, such as humans, monkeys, rabbits, dogs, cats, cows, horses, pigs, mice and rats, suffering from cancer. Preferably, the patient is a human patient, such as an adult human patient. For example, in one embodiment, the subject has a high risk of developing metastatic cancer, such as a patient having a familiar disposition for metastatic cancer. In one embodiment, the subject is a cancer patient who has undergone surgical, medical, and/or radiation anti-cancer therapy without showing clinical signs of metastatic disease.

The cancer can be selected from solid tumours and non-solid tumours. Preferably, the cancer is a nNav1.5-expressing cancer or known to be associated with a risk for increased nNav1.5 expression, metastatic behaviour, invasiveness, aggressiveness, or any combination thereof. In some embodiments, the cancer is a carcinoma. In some embodiments, the cancer is a cancer of a tissue selected from the lung, prostate, stomach, breast, large intestine, rectum, ovary, pancreas, liver, and CNS, such as the brain. In a particular embodiment, the cancer is cancer of the breast or colon or ovary. In another particular embodiment, the cancer is selected from the group consisting of colorectal cancer, breast cancer, lung cancer, ovarian cancer, neuroblastoma and astrocytoma, or a combination of any thereof. Preferably, the cancer is a VGSC-expressing cancer. In some embodiments, the cancer expresses a $nNa_v1.5$.

As used herein, "treating" or "treatment" of a cancer includes, but is not limited to, reducing metastatic behaviour of a cancer, reducing pain sensation, preventing metastatic behaviour of a cancer, reducing pain sensation, reducing the invasiveness of a cancer, reducing the overall aggressiveness of the cancer, or any combination thereof. So, in separate and specific embodiments, a method of treatment according to the invention may (i) reduce metastatic behaviour of the cancer, (ii) prevent metastatic behaviour of the cancer, (iii) reduce pain sensation in a patient suffering from the cancer, (iv) reduce the invasiveness of the cancer, or (v), and combination of two or more of (i) to (iv).

Progression of metastatic cancer, such as breast, colon and prostate cancer, is generally considered as comprising at least some of five main phases, as follows:

1. Genesis, namely the initial transformation of a normal cell into a cancer cell;

2. Proliferation, namely increase in the number of cancer cells to form a primary tumour of increasing size, typically with a smooth and well defined surface;
3. Switching, during the genesis or proliferation phase, from a condition in which the cancer cells have no potential for invasive or metastatic behaviour to a condition in which they do, typically characterised by a dissolving and diffuse boundary of the cancer;
4. Detachment of cancer cells from the primary tumour followed by movement of those detached cells into surrounding regions of tissue within the same organ towards the circulation system (blood and/or lymph);
5. Metastasis, namely the movement of the detached cells through the circulation (blood or lymph) to other organs to create secondary tumours in those other organs.

It should be noted, however, that metastasis may occur without an initial proliferative phase. In such cases, metastases may be found in a patient without an identifiable primary tumour.

By "reducing metastatic behaviour" of cancer, it is intended a reduction of any behaviour associated with the movement of detached cancer cells through the circulation (blood or lymph) to accumulate and/or create secondary tumours in other organs or locally invade surrounding tissues. Typically, the patient is in phase 3, 4 or 5, such as in phase 4 or 5. Reducing metastatic behaviour may, for example, include one or more of (i) reducing transcription, translation and/or expression of nNav1.5 in cancer cells as compared to a control; (ii) reducing cancer cell invasiveness; (iii) reduce peak VGSC current density in cancer cells; (iv) reduce the proportion of cancer cells demonstrating VGSC currents; (v) reducing cancer cell motility (e.g., reduced lateral motility), (vi) reducing cancer cell migration (e.g., transverse migration), and (vii) reducing the persistent part of the VGSC current without eliminating the transient part. "Motility" reflects the ability of the tumour cells to initially move to and through the basement membrane into the surrounding tissue; "invasiveness" of the cells reflects the ability of tumour cells which have entered the surrounding tissue to move through that tissue towards the circulation system; and "migration" reflects the ability of the tumour cells to migrate from that tissue into the circulatory system via the walls thereof.

By "reducing the risk for metastatic cancer" or "preventing metastatic behaviour" of cancer, it is intended to refer prophylactic treatment of a cancer patient at risk for, but not yet diagnosed with, a metastatic disease, so as to prevent or reduce the risk for a metastatic behaviour of the cancer as described above. Typically, the patient is in phase 1, 2 or 3.

The term "benign state" as used herein refers to a tumour or cancer in phase 1 or 2. As used herein, tumours may also or alternatively be characterized as being in a benign state if they (a) do not invade nearby tissue (invasiveness); (b) do not metastasize (spread) to other parts of the body; (c) tend to have clear boundaries; and/or (d) grow slowly.

The term "malignant state" herein refers to a tumour or cancer in phase 3, 4 or 5.

By "reducing the overall aggressiveness of a cancer", it is intended a reduction of any behaviour associated with the progression of cancer, in quantitative or qualitative terms. In some embodiments, reducing the aggressiveness of a cancer refers to the reversal of a cancer in any one of phase 3, 4 or 5 to a lower-number phase, including, but not limited to, from phase 3 to phase 2 or lower, from phase 4 to phase 3 or lower, and from phase 5 to phase 4 or lower. In some embodiments, reducing the aggressiveness of a cancer refers to the reversal of a cancer or tumour in a malignant state to a cancer or tumour in a benign state. In some embodiments, by "reducing the overall aggressiveness of a cancer", it is intended a reduction of a cancer to non-metastatic but not necessarily non-invasive state.

By "reducing the invasiveness of a cancer", it is intended a significant reduction of the invasiveness of the cancer cells under predetermined conditions, e.g., normoxic or hypoxic conditions. Examples of assays suitable to determine invasiveness are provided elsewhere herein (see, e.g., the section entitled "Functional characteristics"). A significant reduction of invasiveness includes, e.g., a reduction by at least about 10%, 20% or more, such as by at least 30%, 40%, 50%, 60%, 70% or 80% as compared to a control.

In some embodiments of the methods of the invention, the binding molecule is administered in a therapeutically effective amount or dose. By "therapeutically effective amount", "therapeutically effective dose", it is intended an amount or dosage of binding molecule that, when administered to a patient suffering from cancer brings about a positive therapeutic response with respect to treatment of the patient, such as, e.g., reduction of metastatic behaviour of the cancer, prevention of metastatic behaviour of the cancer, reduction of pain, or the like.

The binding molecule is administered to the patient in a therapeutically effective amount for the intended purpose, and with a frequency and for a period of time determined by a trained physician. Estimates of effective dosages and in vivo half-lives for the individual binding molecules encompassed by the invention can be made using conventional methodologies or on the basis of in vivo testing using an appropriate animal model.

The binding molecule can be formulated in a composition, typically a pharmaceutical composition, for administration by any suitable route to the patient, including, but not limited to, oral, buccal, sublabial, sublingual, rectal, intravenous, subcutaneous, intradermal, intramuscular, transdermal and intranasal administration and/or direct administration to a tumour, such as a primary tumour. Delivery can, for example, be performed by systemic administration or local administration (e.g., to a tumor), of a composition, such as a pharmaceutical composition, comprising the binding molecule to a subject, e.g., a cancer patient. In some embodiments, the pharmaceutical composition is administered via injection or infusion to the subject, e.g., a cancer patient. In some embodiments, the composition is administered by direct administration into a tumor mass.

In some embodiments, one or more tumours in the patient are hypoxic or are at risk for being hypoxic. In some embodiments, one or more tumours in the patient are expected or determined by the trained physician to be hypoxic. The presence of hypoxia can be determined by a variety of techniques known in the art, including, but not limited to, magnet resonance (MR) imaging (see, e.g., Abadjian et al., Adv Exp Med Biol. 2017; 1036:229-257) or staining a sample of tumour tissue with pimonidazole (see, e.g., Wilson and Hay, Nature Reviews Cancer 2011; 11: 393-410).

In some embodiments, the patient is suffering from a cancer comprising nNav1.5-expressing cancer cells. Such a cancer may, for example, be identified by immunohistochemical or analysis of a cancer cell-containing sample (such as a tumour biopsy or blood sample) obtained from the patient, using detectable monoclonal or polyclonal antibodies specific for nNav1.5 to detect the expression of Nav1.5 by the cancer cells. Advantageously, a detectable monoclonal antibody or antigen-binding fragment thereof can be used for this purpose.

In some embodiments, the treatment methods described herein comprises a step of determining that the cancer comprises cells expressing nNav1.5, typically conducted prior to administering the binding molecule. This can be performed by taking a sample from a tumour in the subject contemplated for treatment, e.g., a tumour biopsy, and analysing the tumour sample or tumour cells for the relevant nNav1.5 mRNA, expression of nNav1.5 protein, or both. Suitable assays for doing this are described elsewhere herein. In a preferred embodiment, the treatment method comprises a step of determining that the cancer comprises cells expressing nNav1.5 prior to administering the binding molecule.

In some embodiments, the therapeutic use or method according to any aspect or embodiment herein is in combination with a second therapeutic agent. In some embodiments, said second therapeutic agent is ranolazine or eleclazine. Suitable dosages of ranolazine and eleclazine can be found in WO2012/049440 (Celex Oncology Ltd.) and WO 2018/146313 (Celex GmbH), both of which are hereby incorporated by reference in their entireties. In some embodiments, the cancer comprises a hypoxic tumor.

In one embodiment, a nNav1.5-expressing cancer is in phase 3, 4 or 5 as described above.

In one embodiment, the patient is in phase 3, 4 or 5, such as in phase 4 or 5.

In one embodiment, the cancer is in phase 1, 2, or 3, such as in phase 1 or 2.

In one embodiment, the cancer is in phase 3. A patient suffering from a cancer in phase 3 has typically not been diagnosed with metastatic disease, but is at risk for metastatic behaviour of the cancer, i.e., progression to phase 4 or 5. A patient suffering from a cancer in phase 3 may thus be treated according to the invention to reduce the risk for metastatic behaviour of the cancer.

In one embodiment, the cancer is in phase 4. A patient suffering from a cancer in phase 4 may not have been diagnosed with metastatic disease, but the cancer has progressed towards metastatic behaviour. A patient suffering from a cancer in phase 4 may thus be treated according to the invention to reduce metastatic behaviour of the cancer.

In one embodiment, the cancer is in phase 5. A patient suffering from a cancer in phase 5 may have been diagnosed with metastatic disease, and the cancer is characterized by metastatic behaviour. A patient suffering from a cancer in phase 5 may thus be treated according to the invention to reduce metastatic behaviour of the cancer.

In some embodiments, a patient may be suffering from a cancer associated with a risk for nNav1.5-expression and/or metastasis or metastatic behaviour, but nNav1.5-expression and/or metastatic behaviour has not yet been determined. Cancers that are prone to metastatic behaviour include, for example, colon cancer, breast cancer, lung cancer, prostate cancer and ovarian cancer. For example, an in vivo diagnostic method according to the invention may not have detected a localised dense signal in a part of the body of the subject indicative of the presence of metastatic disease in said part of the body. Alternatively, immunohistochemical analysis of a biological sample, such as a cancer cell-containing sample, e.g., a tumour biopsy or blood sample obtained from the patient, may not have indicated that the tumour cells in the sample express nNav1.5. The cancer may thus be in phase 1 or (more likely) in phase 2.

In one embodiment, the cancer is in phase 2. A patient suffering from a cancer in phase 2 has typically not been diagnosed with metastatic disease, but is at risk for nNav1.5 expression and metastatic behaviour of the cancer, i.e., progression to phase 3, 4 or higher. A patient suffering from a cancer in phase 2 may thus be treated according to the invention to prevent nNav1.5-activity or metastatic behaviour of the cancer.

A patient suffering from a cancer in any one of phase 1-5, such as in any one of 2-5, may also suffer from pain caused by the cancer, e.g., by a primary tumour, and may thus be treated according to the invention to reduce pain sensation.

In one embodiment, when used in a method according to the invention, the binding molecule reduces or prevents metastatic behaviour in nNav1.5-expressing cancer without killing the cancer cells.

In one embodiment, treatment of cancer cells with the binding molecule results in the VGSC activity of nNav1.5 of the cancer cell, e.g., the VGSC current, being significantly lower than that of a control, such as a predetermined control value, cancer cells not exposed to the binding molecule or cancer cells exposed to a reference compound, e.g., antibody against an irrelevant antigen. In one embodiment, treatment of cancer cells with the binding molecule results in the invasiveness, motility and/or ability to migrate of cancer cells treated with the binding molecule being significantly lower than that of a control, such as a predetermined control value, cancer cells not exposed to the binding molecule or cancer cells exposed to a selected reference compound.

Further Embodiments

The following are further specific embodiments according to the invention.

1. A monoclonal antibody which specifically binds to neonatal 5'-exon splice variants of the α subunit of Na$_v$1.5 (nNa$_v$1.5).
2. The monoclonal antibody according to embodiment 1, which binds nNa$_v$1.5 with at least 100 times higher binding affinity compared to binding to adult 3'-exon splice variants of the α subunit of Na$_v$1.5 (aNav1.5).
3. The monoclonal antibody according to embodiment 1 or 2, wherein the nNa$_v$1.5 comprises an amino acid sequence that differs from SEQ ID NO: 1 in at least amino acid residue 211, such as in amino acid residues 206, 207, 209, 210, 211, 215, and 234.
4. The monoclonal antibody according to embodiment 3, wherein the nNa$_v$1.5 comprises amino acid residues V, S, N, I, K, L, and P in positions 206, 207, 209, 210, 211, 215, and 234 respectively, and where aNav1.5 comprises the amino acid residues T, T, F, V, D, V, and S in the same/corresponding positions.
5. The monoclonal antibody according to any one of the preceding embodiments, where the nNa$_v$1.5 is human nNa$_v$1.5.
6. The monoclonal antibody according to any one of the preceding embodiments, which binds to an epitope in nNa$_v$1.5, which has the residue Lys (K) in position 211.
7. The monoclonal antibody according to any one of the preceding embodiments, where all constant domains, framework regions, or constant and framework regions, are human.
8. The monoclonal antibody according to embodiment 7, which is chimeric, humanized, or fully human.
9. An antigen-binding fragment of the monoclonal antibody according to embodiment 8.

10. A chimeric antigen receptor (CAR) comprising a binding portion which specifically binds to neonatal 5'-exon splice variants of the α subunit of Na$_v$1.5 (nNa$_v$1.5), a transmembrane domain and an endodomain.

11. The CAR of embodiment 10, wherein the binding portion comprises an antigen-binding fragment of a monoclonal antibody.

12. The CAR of embodiment 11, wherein the monoclonal antibody is a monoclonal antibody according to any one of embodiments 1 to 8.

13. The CAR of any one of embodiments 11 and 12, wherein the antigen-binding fragment is a single-chain Fv (scFv) fragment or a Fab fragment.

14. The CAR according to any one of embodiments 10 to 13, wherein at least one of the CAR, the monoclonal antibody and the antigen-binding fragment binds nNa$_v$1.5 with at least 100 times higher binding affinity compared to binding to adult 3'-exon splice variants of the α subunit of Na$_v$1.5 (aNav1.5).

15. The CAR according to any one of embodiments 10 to 14, wherein the nNa$_v$1.5 comprises an amino acid sequence that differs from SEQ ID NO: 1 in at least amino acid residue 211, such as in amino acid residues 206, 207, 209, 210, 211, 215, and 234.

16. The CAR according to embodiment 15, wherein the nNa$_v$1.5 comprises amino acid residues V, S, N, I, K, L, and P in positions 206, 207, 209, 210, 211, 215, and 234 respectively, and where aNav1.5 comprises the amino acid residues T, T, F, V, D, V, and S in the same/corresponding positions.

17. The CAR according to any one of embodiments 10 to 16, where the nNa$_v$1.5 is human nNa$_v$1.5.

18. The CAR according to any one of embodiments 10 to 17, which binds to an epitope in nNa$_v$1.5, which has the residue Lys (K) in position 211.

19. The CAR according to any one of embodiments 10 to 18, wherein the endodomain comprises a signalling domain derived from a T cell receptor molecule, such as the CD3-(CD3-zeta) chain.

20. The CAR according to embodiment 19, wherein the endodomain further comprises one or more co-stimulatory molecules comprising at least one of CD27, CD28, 4-IBB and OX40.

21. The CAR according to any one of embodiments 10 to 20, wherein the transmembrane domain and the most membrane-proximal portion of the endodomain are derived from the same molecule.

22. The CAR according to any one of embodiments 10 to 21, comprising a linker peptide fused to the binding domain and the transmembrane domain.

23. The CAR according to embodiment 10 to 22, wherein the linker peptide comprises the hinge portion of the constant region of an immunoglobulin, such as IgG1 or IgG4.

24. The monoclonal antibody of any one of embodiments 1 to 8, the antigen-binding fragment of embodiment 9, or the CAR of any one of embodiments 10 to 23, which comprises
   (a) variable heavy (VH) complementary-determining regions (CDRs) 1, 2 and 3 and variable light (VL) CDRs 1, 2 and 3 of clone A3;
   (b) VH CDRs 1, 2 and 3 and VL CDRs 1, 2 and 3 of subclone A3-2; or
   (c) VH CDRs 1, 2 and 3 and VL CDRs 1, 2 and 3 of subclone C2-2.

25. The monoclonal antibody, antigen-binding fragment or CAR of embodiment 24, which comprises
   (a) a VH region at least 80%, such as at least 90%, 95%, 97%, 98% or 99% identical, to a VH of clone A3, and a VL region at least 80%, such as at least 90%, 95%, 97%, 98% or 99% identical, to a VL of clone A3;
   (b) a VH region at least 80%, such as at least 90%, 95%, 97%, 98% or 99% identical, to a VH of subclone A3-2, and a VL region at least 80%, such as at least 90%, 95%, 97%, 98% or 99% identical, to a VL of subclone A3-2; or
   (c) a VH region at least 80%, such as at least 90%, 95%, 97%, 98% or 99% identical, to a VH of subclone C2-2, and a VL region at least 80%, such as at least 90%, 95%, 97%, 98% or 99% identical, to a VL of subclone C2-2.

26. The monoclonal antibody, antigen-binding fragment or CAR of any one of embodiments 24 and 25, which comprises
   (a) a VH region comprising a VH of clone A3 and a VL region comprising a VL of clone A3;
   (b) a VH region comprising a VH of subclone A3-2 and a VL region comprising a VL of subclone A3-2;
   (c) a VH region comprising a VH of subclone C2-2 and a VL region comprising a VL of subclone C2-2; or
   (d) the heavy chain and light chain of any one of clone A3, subclone A3-2 and subclone C2-2.

27. A monoclonal antibody, antigen-binding fragment or CAR which competitively inhibits a monoclonal antibody according to embodiment 26 from specifically binding to neonatal 5'-exon splice variants of the α subunit of Na$_v$1.5 (nNa$_v$1.5).

28. A monoclonal antibody, antigen-binding fragment or CAR which specifically binds to the same epitope on neonatal 5'-exon splice variants of the α subunit of Na$_v$1.5 (nNa$_v$1.5) as a monoclonal antibody according to embodiment 26.

29. The monoclonal antibody, antigen-binding fragment or CAR according to any one of embodiments 1 to 28, which specifically binds to a nNa$_v$1.5 comprising the peptide VSENIKLGNLSALR, corresponding to residues 206 to 219 of SEQ ID NO:2.

30. The monoclonal antibody, antigen-binding fragment or CAR according to any one of embodiments 1 to 28, which specifically binds to a neonatal 5'-exon splice variants of the α subunit of Na$_v$1.5 (nNa$_v$1.5) comprising SEQ ID NO:2.

31. A bispecific antibody comprising a first antigen-binding domain which specifically binds to nNa$_v$1.5 and a second antigen-binding domain.

32. The bispecific antibody according to embodiment 24, wherein the first antigen-binding domain comprises the features of the monoclonal antibody according to any one of embodiments 1 to embodiments 1 to 9 or 24 to 31.

33. The bispecific antibody according to any one of embodiments 31 to 32, wherein the second antigen-binding domain specifically binds to sodium-hydrogen exchanger protein (NHE1).

34. A nucleic acid sequence encoding the monoclonal antibody, antigen-binding fragment, CAR, or bispecific antibody of any one of embodiments 1 to 33.

35. An expression vector comprising the nucleic acid sequence of embodiment 34.

36. A T cell or NK cell comprising the nucleic acid sequence of embodiment 34 or the expression vector of embodiment 35.

37. A T cell or NK cell comprising a CAR according to any one of embodiments 10 to 30.

38. A monoclonal antibody according to any one of embodiments 1-8 and 24-29, an antigen-binding fragment according to any one of embodiments 9 and 24 to 30, a bispecific antibody according to any one of embodiments 31 to 33, or a T cell or NK cell according to any one of embodiments 36 and 37, for use as a medicament.

39. A monoclonal antibody according to any one of embodiments 1-8 and 24-29, an antigen-binding fragment according to any one of embodiments 9 and 24 to 30, a bispecific antibody according to any one of embodiments 31 to 33, or a T cell or NK cell according to any one of embodiments 36 and 37, for use in treating cancer.

40. A method for treatment or amelioration of metastatic cancer, comprising administering an effective amount of a monoclonal antibody according to any one of embodiments 1-8 and 24-29, an antigen-binding fragment according to any one of embodiments 9 and 24 to 30, a bispecific antibody according to any one of embodiments 31 to 33, or a T cell or NK cell according to any one of embodiments 36 and 37, to a patient suffering from metastatic cancer.

41. A method for reducing the risk for metastatic cancer in a subject, comprising administering an effective amount of a monoclonal antibody according to any one of embodiments 1-8 and 24-29, an antigen-binding fragment according to any one of embodiments 9 and 24 to 30, a bispecific antibody according to any one of embodiments 31 to 33, or a T cell or NK cell according to any one of embodiments 36 and 37, to said subject.

42. A method for detecting the presence of metastatic cancer in a subject, the method comprising administering a labelled antibody or antigen-binding fragment thereof, which specifically recognizes nNa$_v$1.5, to the subject and subsequently measuring signal distribution derived from the labelled antibody or antigen-binding fragment in said subject, where a localised dense signal in a part of the body of the subject is indicative of the presence of metastatic disease in said part of the body.

43. A method for detecting the presence of neonatal 5'-exon splice variants of the α subunit of Na$_v$1.5 (nNa$_v$1.5) in a biological sample from a subject, the method comprising contacting the biological sample with an antibody or antigen-binding fragment thereof which specifically recognizes nNa$_v$1.5, and subsequently detecting binding of the antibody or antigen-binding fragment to the biological sample.

44. The method according to any one of embodiments 39 to 42, wherein the subject is selected from the group consisting of
a subject having a high risk of developing metastatic cancer, such as a patient having a familiar disposition for metastatic cancer and
a cancer patient who has undergone surgical, medical, and/or radiation anti-cancer therapy without showing clinical signs of metastatic disease.

45. The method according to any one of embodiments 39 to 44, wherein the cancer is selected from solid tumours and non-solid tumours.

46. The method according to any one of embodiments 39 to 45, wherein the cancer is a cancer of a tissue selected from the lung, prostate, stomach, breast, large intestine, rectum, ovary, pancreas, liver, and CNS, such as the brain.

47. The method according to embodiment 46, wherein the cancer is cancer of the breast or colon or ovary.

48. The method according to any one of embodiments 39 to 47, wherein the cancer is colorectal cancer, breast cancer, lung cancer, prostate cancer, ovarian cancer, neuroblastoma or astrocytoma, or a combination of any thereof.

49. The monoclonal antibody according to any one of embodiments 1-8 and 24-30, the antigen binding fragment according to any one of embodiments 9 and 24-30, a bispecific antibody according to any one of embodiments 33 to 35, or a T cell or NK cell according to any one of embodiments 36 and 37 for use in a method according to any one embodiments 38 to 44.

The invention is further illustrated by the following Example, which should not be interpreted as limiting.

EXAMPLES

Example 1—Monoclonal Antibodies Against nNav1.5

Briefly, the peptide described in Chioni et al., (2005); NH$_2$-VSENIKLGNLSALRC-amide (SEQ ID NO:5), herein referred to as "NESO peptide", was used as the immunizing peptide in laboratory mice. Hybridomas were obtained using standard hybridoma technology (NS0 cell line murine myeloma cells), and the following clones/subclones prepared (murine IgG1 kappa antibodies):

Clone 7/Subclone: 7-88

Clone 58/Subclone: 58-39

Clone A3/Subclone: A3-2

Clone C2/Subclone: C2-2

The mAb candidates from these clones/subclones were evaluated by peptide-based and cell-based ELISAs. The former incorporated the original immunizing peptide. The latter employed the human breast cancer MDA-MB-231 cells (Fraser et al., 2005).

Additionally, immunocytochemical tests of the mAbs were carried out using a pair of EBNA-293 cell lines stably expressing nNav1.5 and aNav1.5, described in Chioni et al. (2005). See FIG. 2 for the results.

Further Details can be Found Below.

1. Immunization

1. Two Balb/c mice (M904 and M906) were immunized using the nNav1.5-specific peptide used earlier for the production of the polyclonal antibody, NESOpAb (Chioni et al., 2005). About 10 mg of peptide was synthesized with purity of >80. Of this, 3-4 mg of peptide was conjugated to a carrier protein (ovalbumin, KLH or other).

2. Mice were immunized according to the protocol shown in Table 2.

TABLE 2

| Immunization protocol | |
| --- | --- |
| DAY | Procedure |
| 1 | 100 µg carrier-conjugated peptide + Complete Freund's Adjuvant Intraperitoneal injection |
| 21 | 50 µg carrier-conjugated peptide + Incomplete Freund's Adjuvantn Intraperitoneal injection |

TABLE 2-continued

Immunization protocol

| DAY | Procedure |
|---|---|
| 35 | 50 μg carrier-conjugated peptide + Incomplete Freund's Adjuvant Intraperitoneal injection |
| 49 | 50 μg carrier-conjugated peptide + Incomplete Freund's Adjuvant Intraperitoneal injection |
| 63 | 100 μg carrier-conjugated peptide + Incomplete Freund's Adjuvant Intravenous injection |

2. Cell Fusion

Three days after the final intravenous injection, mice were sacrificed by cervical dislocation. Prior to sacrificing, blood was collected from each mouse and serum was analyzed by ELISA, confirming positivity for the binding with the immobilized antigen.

1. Spleens were surgically resected. Cell fusion was performed, according to the standard method of Kohler and Milstein (1975). Spleens of both M904 and M906 were used.
2. To obtain spleen cell suspension, spleens were minced in a sterile Petri dish, using a surgical scalpel, then they were homogenized in 2 ml of DMEM culture medium (Euroclone) using a glass tissue homogenizer.
3. B-lymphocytes isolated from a spleen after the homogenization procedure were fused with aminopterin sensitive myeloma cells (NS0) using the polyethylene glycol (PEG) method (Galfre and Milstein, 1981).
4. NS0 cells were maintained in logarithmic phase growth for 7 days before cell fusion. An equal number ($10^8$ cells) of B-lymphocytes and NS0 cells were mixed together in 30 ml of DMEM+4 mM L-Gln and centrifuged at 700 g for 5 min. Supernatant was discarded and the tube with cell pellet was placed in a beaker with 37° C. water.
5. The cell fusion protocol was as follows:
   Add 1 ml of 37° C. preheated PEG in 1 minutes, stirring;
   Stir for 2 minutes;
   Add 1 ml of 37° C. preheated DMEM+4 mM L-Gln in 1 minutes, stirring;
   Repeat above;
   Add 1 ml of 37° C. preheated DMEM+4 mM L-Gln in 30 sec, stirring;
   Repeat above;
   Add 6 ml of 37° C. preheated DMEM+4 mM L-Gln in 2 minutes, stirring;
   Add 12 ml of 37° C. preheated DMEM+4 mM L-Gln drop to drop, stirring;
   Centrifuge at 800 g for 5 minutes and discard supernatant.
6. The fusion product was resuspended in DMEM+4 mM L-Gln supplemented with 20% FetalClone I serum (Hyclone) and HAT, (Hypoxanthine, Aminopterine, Timidine) (Sigma).

B-cell/NS0 hybrid selection requires the use of a selective agent, added to the medium, which is HAT. HAT contributes to selection, exploiting the following mechanism: NS0 myeloma cells lack the expression of Hypoxanthine-Guanine PhosphoRibosyl Transferase (HGPRT) enzyme. HGPRT is an enzyme that catalyses the conversion of hypoxanthine to inosine monophosphate and guanine to guanosine monophosphate, transferring the 5-phosphoribosyl group from 5-phosphoribosyl 1-pyrophosphate (PRPP) to the purine, thus playing a central role in the generation of purine nucleotides through the purine salvage pathway. Cells that do not express this enzyme can produce purine nucleotides only through the de novo pathway; but the latter is blocked by aminopterin.

7. The cell fusion product was resuspended in 48 ml of selective complete DMEM medium (supplemented with the selective agent HAT) and aliquoted, according to the following dilutions 1:2, 1:4, 1:8 and 1:8 in 24-well multi-well plates (2 ml for well), labelled as follows:
   M904, dilution 1:2
   M904, dilution 1:4
   M904, dilution 1:8A
   M904, dilution 1:8B
   M906, dilution 1:2
   M906, dilution 1:4
   M906, dilution 1:8A
   M906, dilution 1:8B
8. The plates were incubated in a humidified incubator (37° C., 5% $CO_2$). After two weeks, the selected hybridomas formed visible colony-like clusters.
9. Hybridoma colonies derived from 1:2 and 1:4 dilutions were grown. Supernatant (1 ml) was collected from each well and analyzed for their capacity to bind the antigen by Enzyme-Linked Immunosorbent Assay (ELISA) in order to select the best population for soft agar cloning.

3. Initial Screening

1. Hybridoma supernatants (x96) collected from dilutions 1:2 and 1:4 of both M904 and M906 were analyzed by peptide-based ELISA (enzyme linked immunosorbent assay) to assess the binding to the immobilized antigen.
2. ELISA assay was performed using nNav1.5-peptide, previously employed for the immunization, as antigen. The antigen was diluted to 10 μg/ml in 100 mM $Na_2CO_3$ buffer and aliquoted 100 μl/well in a 96-well plate. After incubation overnight at 4° C., wells were quenched by addition of 200 μl/well blocking solution (3% BSA in 0.05% Tween-20 in PBS) and rested for one hour at room temperature. After further washing, each supernatant was dispensed in duplicate, 100 μl/well. After incubation for two hours at room temperature and washing, anti-mouse secondary antibody diluted in blocking solution 1:500 (10 μg/ml) was dispensed 100 μl/well and incubated for one hour at room temperature. The assay reaction was developed by addition of 100 μl/well TMB (3,3',5,5'-Tetramethylbenzidine) substrate. The reaction was stopped with 100 μl/well 0.5 M HCl. Plates were analyzed measuring the absorbance at 450 nm.
3. 16 positive clones (OD450≥0.8) were obtained; of these, 7 clones were strongly positive (OD450≥1) (Table 3).

TABLE 3

| Serial No. | MOUSE | CLONE | DILUTION | OD450 |
|---|---|---|---|---|
| 1 | M904 | A1 | 1:2 | 0.881 |
| 2 | M904 | A2 | 1:2 | 0.865 |
| 3 | M904 | A3 | 1:2 | 1.250 |
| 4 | M904 | A4 | 1:2 | 2.006 |
| 5 | M904 | A6 | 1:2 | 0.892 |
| 6 | M904 | B1 | 1:2 | 0.845 |
| 7 | M904 | B6 | 1:2 | 0.868 |
| 8 | M904 | C1 | 1:2 | 0.858 |
| 9 | M904 | C2 | 1:2 | 1.967 |
| 10 | M904 | C5 | 1:2 | 1.830 |

TABLE 3-continued

| Serial No. | MOUSE | CLONE | DILUTION | OD450 |
|---|---|---|---|---|
| 11 | M904 | D1 | 1:2 | 1.151 |
| 12 | M904 | D2 | 1:2 | 0.879 |
| 13 | M904 | D5 | 1:2 | 1.853 |
| 14 | M904 | C2 | 1:4 | 0.836 |
| 15 | M904 | C5 | 1:4 | 0.950 |
| 16 | M904 | D4 | 1:4 | 1.636 |
| 17 | M906 | A3 | 1:8A | 1.603 |
| 18 | M906 | C2 | 1:8A | 1.075 |
| 19 | M906 | A6 | 1:8B | 1.422 |

4. A further dilution (1:8) was also tested on supernatants (divided into two plates, A and B).

From these, 3 Clones Emerged as Strongly Positive (OD450≥1):

M906-A3-1:8A (1.603)

M906-C2-1:8A (1.075)

M906-A6-1:8B (1.422)

(Table 1)

5. All 19 positive clones were amplified in flasks. Supernatants were collected and frozen.

4. Cell-Based ELISA Screening on Positive and Negative Clones

1. Cell-based ELISAs were performed on MDA-MB-231 cells by the method of Sette et al. (2013). Cells were seeded and grown to semi-confluence in 96-well plates and incubated overnight in an incubator (37° C., 5% C02).

2. After washing the cells three times with PBS, antibody supernatants were added to the cells and incubated for 2 hours at room temperature. The following steps were as for the peptide-based ELISAs. The results obtained from cell-based ELISA assay on MDA-MB 231 cells are shown in Table 4.

TABLE 4

The table summarizes the results obtained in
cell-based ELISA analyzing 10 clones
(5 positive and 5 negative from peptide-based ELISAs).

| Clone | OD450 |
|---|---|
| BLANK | −0.114 |
| M904-D5-1:2 | 0.274 |
| M904-C2-1:2 | 0.080 |
| M906-A6-1:8B | 0.134 |
| M906-A4-1:8° | 0.095 |
| M904-C1-1:2 | 0.133 |
| M904-C5-1:2 | 0.157 |
| M906-A3-1:8A | 0.676 |
| M906-C2-1:8A | 0.472 |
| M904-D4-1:4 | 0.506 |
| M906-D4-1:8B | 0.168 |

The clones below continued to give positive results both in peptide-based ELISA and cell-based ELISA assay.

M904-D5-1:2

M906-A3-1:8A

M906-C2-1:8A

M904-D4-1:4

Notes:

1) M904-C2-1:2 gave poor absorbance signal in cell-ELISA (while it previously gave positive signal in peptide-based ELISA), probably due to weak confluence of cells in the well.

2) The three clones highlighted in bold, underlined text in Table 4 continuously gave positive results both in peptide-based ELISA and cell-based ELISA.

5. Further Cell-Based Screening

1. Of the 19 clones/supernatants tested on MDA-MB-231 cells, the following 5 gave a good fluorescence signal:

M904-A3-1:2

M904-D5-1:2

M904-C5-1:4

M904-D3-1:2

M906-C2-1:8A.

2. Immunocytochemistry (ICC) assay: Cells were fixed in 2% PFA for 5 min and blocked with 10% swine serum in PBS (pH 7.4) for 1 h. The supernatant (at a given dilution) was applied for 1 h in a moist chamber and washed (3×5 min with washing buffer containing 0.1% BSA in PBS; pH 7.4). The secondary anti-body (FITC-conjugated; diluted 1:50 in 5% swine serum in PBS; pH 7.4) was then applied for 1 h and then washed off, as described above. Finally, cells were washed in distilled H2O and mounted with anti-fading mounting medium (Vectashield, Vector, Burlingame, USA) and visualised with a Zeiss Axioscop-2 fluorescent micro-scope. As a positive control, NESOpAb was used. In negative controls, primary antibody (supernatant) was omitted. All these procedures were performed at room temperature (Chioni et al., 2005).

3. The ICC assay was repeated on MDA-MB-231 for the 5 positive clones and 3 negative clones. Then, the 8 clones were tested on SW620 cells (which also express nNa$_v$1.5) with the same technique. The positive clones that showed a good staining were:

M904-A3-1:2 and

M906-C2-1:8A.

4. The results of the ICC on MDA-MB-231 and SW620 cells are summarized in Table 5. SW620 cells are human colon cancer cells, known to be invasive and to express nNav1.5. Clones that were positive for MDA-MB-231 cells also gave a good signal for SW620 cells.

TABLE 5

| | Immuno-fluorescence intensity MDA-MB-231 | | | | | Immuno-fluorescence intensity SW620 | |
|---|---|---|---|---|---|---|---|
| nNav 1.5 CLONE NAME | IICC | II ICC | III ICC | IV ICC | V ICC | I ICC | II ICC |
| MOUSE 904, A3, 1:2 | ++ | ++ | +++ | ++ | +++ | ++ | +++ |
| MOUSE 904, C1, 1:2 | − | − | − | − | − | − | − |
| MOUSE 904, D5, 1:2 | ++ | + | ++ | ++ | ++ | + | + |
| MOUSE 904, C2, 1:4 | − | − | − | − | − | − | − |
| MOUSE 906, C2, 1:4 | − | − | − | − | − | − | − |

TABLE 5-continued

| nNav 1.5 CLONE NAME | Immuno-fluorescence intensity MDA-MB-231 | | | | | Immuno-fluorescence intensity SW620 | |
|---|---|---|---|---|---|---|---|
| | IICC | II ICC | III ICC | IV ICC | V ICC | I ICC | II ICC |
| MOUSE 904, C5, 1:4 | ++ | ++ | +++ | ++ | | + | + |
| MOUSE 906, C2, 1:8A | ++ | ++ | +++ | + | | ++ | +++ |
| MOUSE 904 D3 1:2 | ++ | + | ++ | ++ | | + | + |

−: complete absence of signal
+: weak intensity
++: moderate intensity
+++: strong intensity 5. The 5 positive clones (for MDA-MB-231) were also tested on transfected EBNA-293 cells expressing neonatal or adult Nav1.5 channel isoform (Table 6).

TABLE 6

| nNav 1.5 CLONE NAME | Immuso-fluorescence intensity EBNA neonatal nNav1.5 | | | immuno-fluorescence intensity EBNA adult nNav1.5 | | |
|---|---|---|---|---|---|---|
| | IICC | II ICC | III ICC | IV ICC | V ICC | I ICC |
| MOUSE 904, A3, 1:2 | +++ | +++ | ++++ | − | + | − |
| MOUSE 904, C1, 12 | − | − | − | − | − | − |
| MOUSE 904, D5, 1:2 | + | + | + | +− | + | + |
| MOUSE 904, C2, 1:4 | − | − | − | − | − | − |
| MOUSE 906, C2, 1:4 | − | − | − | − | − | − |
| MOUSE 904, C5, 1:4 | +++ | + | + | − | + | + |
| MOUSE 906, C2, 1:8A | +++ | +++ | +++ | − | − | − |
| MOUSE 904 D3 1:2 | − | − | + | + | − | + |

−: complete absence of signal

+: weak intensity

++: moderate intensity

+++: strong intensity

6. From the ICC analysis on EBNA cells, it emerged that the following two clones had the best selectivity for neonatal vs. adult Nav1.5:

M904-A3-1:2 and

M906-C2-1:8A

The fluorescence intensity signals for nNav1.5 for these two clones (12±2.5 and 17±2.6 a.u., respectively) were comparable to that obtained with NESOpAb (20±3.5).

These were then subject to PCR amplification and sequencing.

6. PCR Amplification

For the amplification of VH and VL regions (of the A3 clone), a 5' primer that anneals to the VH and VL framework 1 (FR1) (primer forward) and a primer that anneals to the constant region adjacent to VH and VL domains (primer reverse) were chosen. For VL, a degenerate primer able to recognize the kappa light chain was designed. For VH, a 20-base degenerate primer that anneals to the IgG1 heavy chain was designed. The primers used are shown in Table 6 (described originally by Wang et al., 2000).

TABLE 6

| Primer sequences for VH and VL | | |
| --- | --- | --- |
| Target | Primer sequence | SEQ ID NO |
| VH | | |
| Forward (degH1dir) | CAGGTTACTCTGAAAGWGTSTG | 6 |
| Reverse (IgG1rev) | GGAAGATCTATAGACAGATGGGGGTGTCGTTTTGGC | 7 |
| VL | | |
| Forward (degKappadir) | GAYATTGTGMTSACMCARWCTMCA | 8 |
| Reverse (Kapparev) | GGATACAGTTGGTGCAGCATC | 9 |

The amplification reaction of VH and VL was performed with the Phusion. High-25 Fidelity DNA Polymerase (Finnzymes Reagents), following the manufacturer's instructions. The PCR cycles were as shown in Table 7.

TABLE 7

| PCR cycle used for the amplification of VH and VL mRNAs | | | |
| --- | --- | --- | --- |
| Step | Process | Temperature (° C.) | Time (Minutes) |
| 1 | Initial denaturation | 94 | 2 |
| 2 | Denaturation | 94 | 0.5 (30 seconds) |
| 3 | Annealing | 56 (VH) | 1 |
| | | 48 (VL) | 1 |
| 4 | Extension | 72 | 1 |
| 5 | Final extension | 72 | 10 |
| + | Steps 2-4 were repeated 24 times | | |

7. VH and VL Cloning

PCR products relative to VH and VL were run on 1% agarose in TAE buffer (Tris, acetic acid and EDTA), then excised from the gel with a scalpel and purified using QIAquick PCR Purification Kit (QIAGEN), according to the manufacturer's instruction. QIAquick Kits contain a silica membrane assembly for binding of DNA in high-salt buffer and elution with water. The purification procedure removes impurities from DNA samples. After purification from agarose gel, PCR products were cloned into pCR™—Blunt vector (where it is possible to insert blunt PCR products), using a 10:1 molar ratio of insert:vector, according to the following formula: X (ng) insert=(10)(Y bp PCR product) (25 ng linearized pCR™—Blunt)/(3500 bp PCR™—Blunt), where X ng is the amount of PCR product of Y base pairs to be ligated (Ausubel et al., 1994). The ligation reaction was incubated at 25° C. for 15 min. TOP10F cells were used for the transformation step and the selected colonies were checked for the presence of the insert in the right orientation.

8. Sequencing and Analysis of VH and VL

DNA samples were sequenced by Eurofins Genomics and the relative products were analyzed using IMGTTool software in order to find the three scFv Complementary Determining Regions (CDR1, CDR2 and CDR3). 12 colonies for VH and 12 colonies for VL were screened and the results showed that they are equal.

The VH and VL nucleotide sequences (SEQ ID NO:10 and 11, respectively) of the A3 antibody are shown in FIG. 4.

REFERENCES FOR EXAMPLE 1

Ausubel, F. M., Brent, R., Kingston, R. E., Moore, D. D., Seidman, J. G., Smith, J. A., and Struhl, K. (1994). Current Protocols in Molecular Biology (New York: Greene Publishing Associates and WileyInterscience).

Chioni A M, Fraser S P, Pani F, Foran P, Wilkin G P, Diss J K, Djamgoz M B. A novel polyclonal antibody specific for the Na(v)1.5 voltage-gated Na(+) channel 'neonatal' splice form. J Neurosci Methods. 2005 Sep. 30; 147(2): 88-98. doi: 10.1016/j.jneumeth.2005.03.010.

Galfre G, Milstein C. Preparation of monoclonal antibodies: strategies and procedures. Methods Enzymol. 1981; 73(Pt B):3-46. doi: 10.1016/0076-6879(81)73054-4.

Kohler G, Milstein C. Continuous cultures of fused cells secreting antibody of predefined specificity. Nature. 1975 Aug. 7; 256(5517):495-7. doi: 10.1038/256495α0.

Sette A, Spadavecchia J, Landoulsi J, Casale S, Haye B, Crociani O, Arcangeli A. doi: 10.1007/s11051-013-2111-6.

Wang Z, Raifu M, Howard M, Smith L, Hansen D, Goldsby R et al. Universal PCR amplification of mouse immunoglobulin gene variable regions: the design of degenerate primers and an assessment of the effect of DNA polymerase 3' to 5' exonuclease activity, J Immunol Methods 2000; 233:167-77.

| SEQUENCE TABLE | |
| --- | --- |
| SEQ ID NO/ Description | Sequence |
| SEQ ID NO: 1 aNav1.5 UniProtKB- Q14524 (SCN5A_HUMAN), | MANFLLPRGTSSFRRFTRESLAAIEKRMAEKQARGSTTLQESREGLPEEEAPRPQLDLQAS KKLPDLYGNPPQELIGEPLEDLDPFYSTQKTFIVLNKGKTIFRFSATNALYVLSPFHPIRR AAVKILVHSLFNMLIMCTILTNCVFMAQHDPPPWTKYVEYTFTAIYTFESLVKILARGFCL HAFTFLRDPWNWLDFSVIIMAYTTEFVDLGNVSALRTFRVLRALKTISVISGLKTIVGALI QSVKKLADVMVLTVFCLSVFALIGLQLFMGNLRHKCVRNFTALNGTNGSVEADGLVWESLD |

-continued

| SEQUENCE TABLE | |
| --- | --- |
| SEQ ID NO/<br>Description | Sequence |
| ISOFORM-1<br>(Nav1.5c)<br>>sp\|Q14524\|<br>SCN5A_HUMAN<br>Sodium channel<br>protein type 5<br>subunit alpha<br>OS = *Homo*<br>*sapiens*<br>Ox = 9606<br>GN = SCN5A PE = 1<br>SV = 2 | LYLSDPENYLLKNGTSDVLLCGNSSDAGTCPEGYRCLKAGENPDHGYTSFDSFAWAFLALF<br>RLMTQDCWERLYQQTLRSAGKIYMIFFMLVIFLGSFYLVNLILAVVAMAYEEQNQATIAET<br>EEKEKRFQEAMEMLKKEHEALTIRGVDTVSRSSLEMSPLAPVNSHERRSKRRKRMSSGTEE<br>CGEDRLPKSDSEDGPRAMNHLSLTRGLSRTSMKPRSSRGSIFTFRRRDLGSEADFADDENS<br>TAGESESHHTSLLVPWPLRRTSAQGQPSPGTSAPGHALHGKKNSTVDCNGVVSLLGAGDPE<br>ATSPGSHLLRPVMLEHPPDTTTPSEEPGGPQMLTSQAPCVDGFEEPGARQRALSAVSVLTS<br>ALEELEESRHKCPPCWNRLAQRYLIWECCPLWMSIKQGVKLVVMDPFTDLTITMCIVLNTL<br>FMALEHYNMTSEFEEMLQVGNLVFTGIFTAEMTFKIIALDPYYYFQQGWNIFDSIIVILSL<br>MELGLSRMSNLSVLRSFRLLRVFKLAKSWPTLNTLIKIIGNSVGALGNLTLVLAIIVFIFA<br>VVGMQLFGKNYSELRDSDSGLLPRWHMMDFFHAFLIIFRILCGEWIETMWDCMEVSGQSLC<br>LLVFLLVMVIGNLVVLNLFLALLLSSFSADNLTAPDEDREMNNLQLALARIQRGLRFVKRT<br>TWDFCCGLLRQRPQKPAALAAQGQLPSCIATPYSPPPPETEKVPPTRKETRFEEGEQPGQG<br>TPGDPEPVCVPIAVAESDTDDQEEDEENSLGTEEESSKQQESQPVSGGPEAPPDSRTWSQV<br>SATASSEAEASASQADWRQQWKAEPQAPGCGETPEDSCSEGSTADMTNTAELLEQIPDLGQ<br>DVKDPEDCFTEGCVRRCPCCAVDTTQAPGKVWWRLRKTCYHIVEHSWFETFIIFMILLSSG<br>ALAFEDIYLEERKTIKVLLEYADKMFTYVFVLEMLLKWVAYGFKKYFTNAWCWLDFLIVDV<br>SLVSLVANTLGFAEMGPIKSLRTLRALRPLRALSRFEGMRVVVNALVGAIPSIMNVLLVCL<br>IFWLIFSIMGVNLFAGKFGRCINQTEGDLPLNYTIVNNKSQCESLNLTGELYWTKVKVNFD<br>NVGAGYLALLQVATFKGWMDIMYAAVDSRGYEEQPQWEYNLYMYIYFVIFIIFGSFFTLNL<br>FIGVIIDNFNQQKKKLGGQDIFMTEEQKKYYNAMKKLGSKKPQKPIPRPLNKYQGFIFDIV<br>TKQAFDVTIMFLICLNMVTMMVETDDQSPEKINILAKINLLFVAIFTGECIVKLAALRHYY<br>FTNSWNIFDFVVVILSIVGTVLSDIIQKYFFSPTLFRVIRLARIGRILRLIRGAKGIRTLL<br>FALMMSLPALFNIGLLLFLVMPFIYSIFGMANFAYVKWEAGIDDMFNFQTFANSMLCLFQIT<br>TSAGWDGLLSPILNTGPPYCDPTLPNSNGSRGDCGSPAVGILFFTTYIIISFLIVVNMYIA<br>IILENFSVATEESTEPLSEDDFDMFYEIWEKFDPEATQFIEYSVLSDFADALSEPLRIAKP<br>NQISLINMDLPMVSGDRIHCMDILFAFTKRVLGESGEMDALKIQMEEKFMAANPSKISYEP<br>ITTTLRRKHEEVSAMVIQRAFRRHLLQRSLKHASFLRQQAGSGLSEEDAPEREGLIAYVM<br>SENFSRPLGPPSSSSISSTSFPPSYDSVTRATSDNLQVRGSDYSHSEDLADFPPSPDRDRE<br>SIV |
| SEQ ID NO: 2<br>nNav1.5<br>(example)<br>UniProtKB-<br>H9KVD2<br>(H9KVD2_HUMAN)<br>>tr\|H9KVD2\|<br>H9KVD2_HUMAN<br>Sodium channel<br>protein<br>OS = *Homo*<br>*sapiens*<br>Ox = 9606<br>GN = SCN5A PE = 1<br>SV = 1 | MANFLLPRGTSSFRRFTRESLAAIEKRMAEKQARGSTTLQESREGLPEEEAPRPQLDLQAS<br>KKLPDLYGNPPQELIGEPLEDLDPFYSTQKTFIVLNKGKTIFRFSATNALYVLSPFHPIRR<br>AAVKILVHSLFNMLIMCTILTNCVFMAQHDPPPWTKYVEYTFTAIYTFESLVKILARGFCL<br>HAFTFLRDPWNWLDFSVIIMAYVSENIKLGNLSALRTFRVLRALKTISVIPGLKTIVGALI<br>QSVKKLADVMVLTVFCLSVFALIGLQLFMGNLRHKCVRNFTALNGTNGSVEADGLVWESLD<br>LYLSDPENYLLKNGTSDVLLCGNSSDAGTCPEGYRCLKAGENPDHGYTSFDSFAWAFLALF<br>RLMTQDCWERLYQQTLRSAGKIYMIFFMLVIFLGSFYLVNLILAVVAMAYEEQNQATIAET<br>EEKEKRFQEAMEMLKKEHEALTIRGVDTVSRSSLEMSPLAPVNSHERRSKRRKRMSSGTEE<br>CGEDRLPKSDSEDGPRAMNHLSLTRGLSRTSMKPRSSRGSIFTFRRRDLGSEADFADDENS<br>TAGESESHHTSLLVPWPLRRTSAQGQPSPGTSAPGHALHGKKNSTVDCNGVVSLLGAGDPE<br>ATSPGSHLLRPVMLEHPPDTTTPSEEPGGPQMLTSQAPCVDGFEEPGARQRALSAVSVLTS<br>ALEELEESRHKCPPCWNRLAQRYLIWECCPLWMSIKQGVKLVVMDPFTDLTITMCIVLNTL<br>FMALEHYNMTSEFEEMLQVGNLVFTGIFTAEMTFKIIALDPYYYFQQGWNIFDSIIVILSL<br>MELGLSRMSNLSVLRSFRLLRVFKLAKSWPTLNTLIKIIGNSVGALGNLTLVLAIIVFIFA<br>VVGMQLFGKNYSELRDSDSGLLPRWHMMDFFHAFLIIFRILCGEWIETMWDCMEVSGQSLC<br>LLVFLLVMVIGNLVVLNLFLALLLSSFSADNLTAPDEDREMNNLQLALARIQRGLRFVKRT<br>TWDFCCGLLRQRPQKPAALAAQGQLPSCIATPYSPPPPETEKVPPTRKETRFEEGEQPGQG<br>TPGDPEPVCVPIAVAESDTDDQEEDEENSLGTEEESSKQQESQPVSGGPEAPPDSRTWSQV<br>SATASSEAEASASQADWRQQWKAEPQAPGCGETPEDSCSEGSTADMTNTAELLEQIPDLGQ<br>DVKDPEDCFTEGCVRRCPCCAVDTTQAPGKVWWRLRKTCYHIVEHSWFETFIIFMILLSSG<br>ALAFEDIYLEERKTIKVLLEYADKMFTYVFVLEMLLKWVAYGFKKYFTNAWCWLDFLIVDV<br>SLVSLVANTLGFAEMGPIKSLRTLRALRPLRALSRFEGMRVVVNALVGAIPSIMNVLLVCL<br>IFWLIFSIMGVNLFAGKFGRCINQTEGDLPLNYTIVNNKSQCESLNLTGELYWTKVKVNFD<br>NVGAGYLALLQVATFKGWMDIMYAAVDSRGYEEQPQWEYNLYMYIYFVIFIIFGSFFTLNL<br>FIGVIIDNFNQQKKKLGGQDIFMTEEQKKYYNAMKKLGSKKPQKPIPRPLNKYQGFIFDIV<br>TKQAFDVTIMFLICLNMVTMMVETDDQSPEKINILAKINLLFVAIFTGECIVKLAALRHYY<br>FTNSWNIFDFVVVILSIVGTVLSDIIQKYFFSPTLFRVIRLARIGRILRLIRGAKGIRTLL<br>FALMMSLPALFNIGLLLFLVMPFIYSIFGMANFAYVKWEAGIDDMFNFQTFANSMLCLFQIT<br>TSAGWDGLLSPILNTGPPYCDPTLPNSNGSRGDCGSPAVGILFFTTYIIISFLIVVNMYIA<br>IILENFSVATEESTEPLSEDDFDMFYEIWEKFDPEATQFIEYSVLSDFADALSEPLRIAKP<br>NQISLINMDLPMVSGDRIHCMDILFAFTKRVLGESGEMDALKIQMEEKFMAANPSKISYEP<br>ITTTLRRKHEEVSAMVIQRAFRRHLLQRSLKHASFLRQQAGSGLSEEDAPEREGLIAYVM<br>SENFSRPLGPPSSSSISSTSFPPSYDSVTRATSDNLQVRGSDYSHSEDLADFPPSPDRDRE<br>SIV |
| SEQ ID NO: 3/<br>Amino acid<br>sequence<br>corresponding to<br>exon 6 of a<br>nNav1.5 | YVSENIKLGNLSALRTFRVLRALKTISVIP |

-continued

| SEQUENCE TABLE | |
| --- | --- |

| SEQ ID NO/<br>Description | Sequence |
| --- | --- |
| SEQ ID NO :4/<br>Partial consensus<br>sequence<br>nNav1.5 and<br>aNav1.5 (FIG. 1) | YVTEFVXLGNVSALRTFRVLRALKTISVIP, wherein "X" is K or D |
| SEQ ID NO: 5/<br>NESO peptide | NH$_2$-VSENIKLGNLSALRC-amide |
| SEQ ID NO: 6<br>VH primer;<br>Forward<br>(degH1dir) | CAGGTTACTCTGAAAGWGTSTG |
| SEQ ID NO: 7<br>VH primer;<br>Reverse<br>(IgG1rev) | GGAAGATCTATAGACAGATGGGGGTGTCGTTTTGGC |
| SEQ ID NO: 8<br>VL primer;<br>Forward<br>(degKappadir) | GAYATTGTGMTSACMCARWCTMCA |
| SEQ ID NO: 9<br>VL primer;<br>Reverse<br>(Kapparev) | GGATACAGTTGGTGCAGCATC |
| SEQ ID NO: 10<br>A3 VH sequence<br>(nucleotide) | CAGGTTACTCTGAAAGTGTCTGGCCCTGGGATATTGCAGCCCTCCCAGACCCTCAGTCTGA<br>CCTGTTCTTTTTCTGGGTTTTCACTGACCACTTCTGGTATGGGTGTGAGCTGGATTCGTCA<br>GGCTGCAGGAAAGGGTCTGGAGTGGCTGGCACACATTTACTGGGATGATGACAAGCGCTAT<br>AACCCAGCCCTGAAGAGCCGGCTCACAATCTCCAAGGATACCTCCAGCAACCAAGTATTCC<br>TCAACATCACCAGTGTGGACACTGCAGATACTGCCACATACTACTGTGCTCGAAGGGAGGA<br>CTATGTTACGAGTTTGCTAAGTGGGGCCAAGGGACTCTGGTCACTGTGTTTG |
| SEQ ID NO: 11<br>A3 VL sequence<br>(nucleotide) | GATATTGTGCTGACCCAGTCTCCTGCTTCCTTAGCTGTATCTCTGGGGCAGAGGGCCAGCA<br>TCTCATACAGGGCCAGCAAAAGTGTCAGTACATCTGGCTATAGTTATATGCACTGGAACCG<br>ACAGAAGCCAGGACAGCCACCCAGACTCCTCATCTATCTTGTATCCAACCTAGAATCTGGG<br>GTCCCTGCCAGGTTCAGTGGCAGTGGGTCTGGGACAGACTTCACCCTCAACATCCATCCTG<br>TGGAGGAGGAGGATGCTGCAACCTATTACTGTCAGCACATTAGGGAGCTTACACGTTCGGA<br>GGGGGGACCAAGCTGGAAATACGAC |
| SEQ ID NO: 12<br>A3 VH sequence<br>(protein) | QVTLKVSGPGILQPSQTLSLTCSFS<u>GFSLTTS</u>GMGVSWIRQAAGKGLEWLAHI<u>YWDDD</u>KRY<br>NPALKSRLTISKDTSSNQVFLNITSVDTADTATYYCAR<u>REDYVTSLL</u>SGAKGLWSLCL |
| SEQ ID NO: 13<br>A3 VL sequence<br>(protein) | DIVLTQSPASLAVSLGQRASISYR<u>ASKSVSTSGYSYMH</u>WNRQKPGQPPRLLIYL<u>VSNLES</u>G<br>VPARFSGSGSGTDFTLNIHPVEEEDAATYYC<u>QHIRELTRSE</u>GGPSWKYD |
| SEQ ID NO: 14<br>VH CDR1 | GFSLTTS |
| SEQ ID NO: 15<br>VH CDR2 | YWDDD |
| SEQ ID NO: 16<br>VH CDR3 | REDYVTSLL |
| SEQ ID NO: 17<br>VL CDR1 | RASKSVSTSGYSYMH |
| SEQ ID NO: 18<br>VL CDR2 | LVSNLES |
| SEQ ID NO: 19<br>VL CDR3 | QHIRELTRSE |

REFERENCES

Each reference cited in the present disclosure or listed below is incorporated by reference, in its entirety.
Brackenbury et al., Cancer Res Treat. 2007 January; 101 (2):149-60. doi: 10.1007/s10549-006-9281-1.
Dotti et al., Immunol Rev. 2014 January; 257(1): doi: 10.1111/imr.12131 Sadelain et al., Cancer Discov. 2013 April; 3(4):388-398. doi:10.1158/2159-8290.CD-12-0548.
Chioni et al., J Neuroscience Methods 2005; 147:88-98.
Fraser et al., Clin Cancer Res 2005; 11:5381-5389.
Fraser et al., Pflugers Archives 2003; 446:559-71.
Grimes et al., FEBS Lett 1995; 369:290-294.
Laniado et al., The Prostate 2001; 46:262-274.
Laniado et al., Am J Pathol 1997; 150:1213-1221.
Onkal et al., J Cell Physiol 2008; 216:716-726.
Brisson et al., J Cell Sci. 2013 Nov. 1; 126(Pt 21):4835-42. doi: 10.1242/jcs.123901. Epub 2013 Jul. 31.
Djamgoz et al., Cancers (Basel). 2019 Oct. 28; 11(11). pii: E1675. doi: 10.3390/cancers 11111675.

---

The invention claimed is:

1. A monoclonal antibody, or an antigen-binding fragment thereof, which specifically binds to neonatal 5'-exon splice variants of the α subunit of Nav1.5 (nNav1.5), comprising a VH region comprising complementarity determining region (CDR) 1, CDR2, and CDR3 amino acid sequences comprising SEQ ID NOs: 14, 15, and 16, respectively, and a VL region comprising CDR1, CDR2, and CDR3 amino acid sequences comprising SEQ ID NOs: 17, 18, and 19, respectively.

2. The monoclonal antibody according to claim 1, which binds to the peptide segment corresponding to residues 206 to 219 of SEQ ID NO:2.

3. The monoclonal antibody according to claim 2, which binds more readily to a nNav1.5 comprising the amino acid sequence of residues 206 to 219 of SEQ ID NO: 2 than to an adult 3'-exon splice variant of the α subunit of Nav1.5 (aNav1.5) comprising the amino acid sequence of residues 206 to 219 of SEQ ID NO:1.

4. The monoclonal antibody according to claim 3, which reduces the VGSC current of a VGSC comprising a nNav1.5.

5. The monoclonal antibody according to claim 4, wherein the nNav1.5 is a human nNav1.5.

6. The monoclonal antibody, or antigen-binding fragment thereof, according to claim 1, comprising a VH region at least 80%, such as at least 90%, 95%, 97%, 98% or 99% identical, to the VH region encoded by SEQ ID NO: 10, and a VL region at least 80%, such as at least 90%, 95%, 97%, 98% or 99% identical, to the VL region encoded by SEQ ID NO: 11.

7. The monoclonal antibody, or antigen-binding fragment thereof, according to claim 1, comprising a VH region comprising the amino acid sequence of SEQ ID NO: 12 and a VL region comprising the amino acid sequence of SEQ ID NO:13.

8. The monoclonal antibody according to claim 1, wherein all constant domains, framework regions, or constant domains and framework regions, are human.

9. The monoclonal antibody according to claim 8, which is chimeric, or humanized.

10. A chimeric antigen receptor (CAR), bispecific antibody, or antibody-drug conjugate (ADC) comprising a monoclonal antibody, or antigen-binding fragment thereof, according to claim 1.

11. A nucleic acid sequence encoding the monoclonal antibody, or antigen-binding fragment thereof, of claim 1.

12. An expression vector comprising the nucleic acid sequence of claim 11.

13. A cell comprising the nucleic acid sequence of claim 11.

14. A method of producing a monoclonal antibody, or antigen-binding fragment thereof, according to claim 1, the method comprising culturing a cell comprising a nucleic acid sequence encoding the monoclonal antibody or the antigen-binding fragment, and recovering the monoclonal antibody or the antigen-binding fragment.

15. A method for treatment or amelioration of metastatic cancer in a subject, comprising administering to the subject an effective amount of a monoclonal antibody, or an antigen-binding fragment thereof, according to claim 1.

16. A method for reducing the risk for metastatic cancer in a subject, comprising administering to the subject an effective amount of a monoclonal antibody, or antigen-binding fragment thereof, according to claim 1.

17. A method for detecting the presence of metastatic cancer in a subject, the method comprising administering a labelled antibody or antigen-binding fragment thereof, which specifically recognizes nNav1.5, to the subject and subsequently measuring signal distribution derived from the labelled antibody or antigen-binding fragment in said subject, where a localised dense signal in a part of the body of the subject is indicative of the presence of metastatic disease in said part of the body, wherein the antibody or antigen-binding fragment thereof is a monoclonal antibody, or antigen-binding fragment thereof, according to claim 1.

18. A method for detecting the presence of neonatal 5'-exon splice variants of the $\alpha$ subunit of Nav1.5 (nNav1.5) in a biological sample from a subject, the method comprising contacting the biological sample with an antibody or antigen-binding fragment thereof which specifically recognizes nNav1.5, and subsequently detecting binding of the antibody or antigen-binding fragment to the biological sample, wherein the antibody or antigen-binding fragment thereof is a monoclonal antibody, or antigen-binding fragment thereof, according to claim 1.

* * * * *